(12) United States Patent
Phillips

(10) Patent No.: US 11,938,231 B2
(45) Date of Patent: Mar. 26, 2024

(54) COMPOSITIONS I-I AND PRODUCTS AND USES THEREOF

(71) Applicant: Smith & Nephew PLC, Watford (GB)

(72) Inventor: Marcus Damian Phillips, Heslington (GB)

(73) Assignee: Smith & Nephew PLC, Watford (GB)

( * ) Notice: Subject to any disclaimer, the term of this patent is extended or adjusted under 35 U.S.C. 154(b) by 0 days.

(21) Appl. No.: 17/093,214

(22) Filed: Nov. 9, 2020

(65) Prior Publication Data

US 2021/0121599 A1 Apr. 29, 2021

Related U.S. Application Data

(60) Division of application No. 16/213,630, filed on Dec. 7, 2018, now abandoned, which is a continuation of application No. 13/989,560, filed as application No. PCT/GB2011/001649 on Nov. 25, 2011, now abandoned.

(30) Foreign Application Priority Data

Nov. 25, 2010 (GB) ..................................... 1020005

(51) Int. Cl.
| | | |
|---|---|---|
| A61L 15/42 | (2006.01) | |
| A61L 15/26 | (2006.01) | |
| A61L 15/58 | (2006.01) | |
| A61L 24/00 | (2006.01) | |
| A61L 26/00 | (2006.01) | |

(52) U.S. Cl.
CPC .............. *A61L 15/425* (2013.01); *A61L 15/26* (2013.01); *A61L 15/58* (2013.01); *A61L 24/0073* (2013.01); *A61L 26/0095* (2013.01)

(58) Field of Classification Search
CPC .......... A61P 17/02; C08L 83/04; A61L 15/26; A61L 15/425; A61L 15/58; A61L 24/0073; A61L 26/0095
See application file for complete search history.

(56) References Cited

U.S. PATENT DOCUMENTS

| | | |
|---|---|---|
| 3,274,155 A | 9/1966 | Saunders et al. |
| 3,646,155 A | 2/1972 | Scott et al. |
| 3,783,870 A | 1/1974 | Schachet |
| 3,808,178 A | 4/1974 | Gaylord et al. |
| 3,809,086 A | 5/1974 | Schachet et al. |
| 3,809,087 A | 5/1974 | Lewis, Jr. |
| 3,928,629 A | 12/1975 | Chandra et al. |
| 3,972,328 A | 8/1976 | Chen |
| 4,029,598 A | 6/1977 | Neisius et al. |
| 4,073,294 A | 2/1978 | Stanley et al. |
| 4,117,551 A | 9/1978 | Brooks et al. |
| 4,266,545 A | 5/1981 | Moss |
| 4,278,089 A | 7/1981 | Huck et al. |
| 4,392,860 A | 7/1983 | Huck et al. |
| 4,529,553 A | 7/1985 | Faltynek |
| 4,538,920 A | 9/1985 | Drake |
| 4,569,674 A | 2/1986 | Phillips et al. |
| 4,578,060 A | 3/1986 | Huck et al. |
| 4,655,754 A | 4/1987 | Richmond et al. |
| 4,661,093 A | 4/1987 | Beck et al. |

(Continued)

FOREIGN PATENT DOCUMENTS

| | | |
|---|---|---|
| CN | 1805761 B | 5/2010 |
| DE | 3443101 A1 | 5/1986 |

(Continued)

OTHER PUBLICATIONS

US 6,216,701 B1, 04/2001, Heaton et al. (withdrawn)
Puleo, John R., et al., Biotechnology and Bioengineering, vol. VIII, Issue 4, pp. 631-632 (1966) (Year: 1966).*
Advantec MFS, Inc., "Membrane Filters" (catalog), retreived from http://www.advantecmfs.com/catalog/filt/membrane.pdf, on Jan. 29, 2016, Copyright 2001-2011, 17 pages.

(Continued)

*Primary Examiner* — Andrew S Rosenthal
*Assistant Examiner* — Lyndsey M Beckhardt
(74) *Attorney, Agent, or Firm* — Knobbe, Martens, Olson & Bear, LLP

(57) ABSTRACT

A curable composition apportioned between at least one Part A and at least one Part B, the Parts sealed within barrier means in manner to prevent contamination thereof, the composition comprising:

(i) one or more alkenyl-containing prepolymers having at least one alkenyl moiety per molecule, (ii) one or more SiH-containing prepolymers having at least one SiH unit per molecule, and additionally:

(iii) a catalyst for curing by addition of alkenyl-containing prepolymer (i) to SiH-containing prepolymer (ii), wherein the at least one Part A and at least one Part B are provided within or upon at least two respective receptacles or supports and are adapted to be dispensed or released therefrom in cooperative manner facilitating intimate contact and curing thereof, wherein the receptacle(s) or support(s) for at least one of Part A and Part B is thermally stable at elevated temperature of 123 C for a period in excess of 18 hours, methods for preparing the composition, methods for sterilisation thereof, medical and non-medical use thereof, a device incorporating the composition, and a precursor therefor including its sterilisable precursor composition, in particular a terminally sterilisable or terminally sterile composition for medical use, particularly in wound therapy, more particularly as a wound packing material which can be shaped and configured to the shape of a wound, most particularly for application in negative pressure wound therapy (NPWT).

13 Claims, 14 Drawing Sheets

(56) References Cited

U.S. PATENT DOCUMENTS

| | | |
|---|---|---|
| 4,713,052 A | 12/1987 | Beck et al. |
| 4,714,739 A | 12/1987 | Arkles |
| 4,720,431 A | 1/1988 | Wong |
| 4,728,499 A | 3/1988 | Fehder |
| 4,753,536 A | 6/1988 | Spehar et al. |
| 4,767,026 A | 8/1988 | Keller et al. |
| 4,771,919 A | 9/1988 | Ernst |
| 4,791,149 A | 12/1988 | Pocknell |
| 4,798,583 A | 1/1989 | Beck et al. |
| 4,813,942 A | 3/1989 | Alvarez |
| 4,826,494 A | 5/1989 | Richmond et al. |
| 4,838,253 A | 6/1989 | Brassington et al. |
| 4,872,450 A | 10/1989 | Austad |
| 4,923,444 A | 5/1990 | Daoud et al. |
| 4,936,834 A | 6/1990 | Beck et al. |
| 4,969,880 A | 11/1990 | Zamierowski |
| 4,991,574 A | 2/1991 | Pocknell |
| 5,004,643 A | 4/1991 | Caldwell |
| 5,010,115 A | 4/1991 | Grisoni |
| 5,033,650 A | 7/1991 | Colin et al. |
| 5,056,510 A | 10/1991 | Gilman |
| 5,064,653 A | 11/1991 | Sessions et al. |
| 5,080,493 A | 1/1992 | McKown et al. |
| 5,089,606 A | 2/1992 | Cole et al. |
| 5,100,395 A | 3/1992 | Rosenberg |
| 5,141,503 A | 8/1992 | Sewell, Jr. |
| 5,145,933 A | 9/1992 | Grisoni et al. |
| 5,153,231 A | 10/1992 | Bouquet et al. |
| 5,181,905 A | 1/1993 | Flam |
| 5,238,732 A | 8/1993 | Krishnan |
| 5,249,709 A | 10/1993 | Duckworth et al. |
| 5,266,326 A | 11/1993 | Barry et al. |
| 5,333,760 A | 8/1994 | Simmen |
| 5,348,392 A | 9/1994 | Bouquet et al. |
| 5,397,848 A | 3/1995 | Yang et al. |
| 5,456,745 A | 10/1995 | Roreger et al. |
| 5,549,584 A | 8/1996 | Gross |
| 5,582,596 A | 12/1996 | Fukunaga et al. |
| 5,583,114 A | 12/1996 | Barrows et al. |
| 5,609,271 A | 3/1997 | Keller et al. |
| 5,612,050 A | 3/1997 | Rowe et al. |
| 5,636,643 A | 6/1997 | Argenta et al. |
| 5,645,081 A | 7/1997 | Argenta et al. |
| 5,660,823 A | 8/1997 | Chakrabarti et al. |
| 5,707,499 A | 1/1998 | Joshi et al. |
| 5,717,030 A | 2/1998 | Dunn et al. |
| 5,747,064 A | 5/1998 | Burnett et al. |
| 5,759,560 A | 6/1998 | Dillon |
| 5,759,570 A | 6/1998 | Arnold |
| 5,776,193 A | 7/1998 | Kwan et al. |
| 5,834,007 A | 11/1998 | Kubota |
| 5,840,777 A | 11/1998 | Eagles et al. |
| 5,852,126 A | 12/1998 | Barnard et al. |
| 5,874,500 A | 2/1999 | Rhee et al. |
| D406,899 S | 3/1999 | Cottle |
| RE36,235 E | 6/1999 | Keller et al. |
| 5,944,703 A | 8/1999 | Dixon et al. |
| 5,945,115 A | 8/1999 | Dunn et al. |
| 5,962,010 A | 10/1999 | Greff et al. |
| 5,998,472 A | 12/1999 | Berger et al. |
| 6,022,904 A | 2/2000 | Sollradl et al. |
| 6,024,731 A | 2/2000 | Seddon et al. |
| 6,065,270 A | 5/2000 | Reinhard et al. |
| 6,071,267 A | 6/2000 | Zamierowski |
| 6,121,341 A | 9/2000 | Sawhney et al. |
| 6,135,116 A | 10/2000 | Vogel et al. |
| D434,150 S | 11/2000 | Tumey et al. |
| 6,142,982 A | 11/2000 | Hunt et al. |
| 6,143,352 A | 11/2000 | Clark et al. |
| 6,165,201 A | 12/2000 | Sawhney et al. |
| 6,168,788 B1 | 1/2001 | Wortham |
| D439,341 S | 3/2001 | Tumey et al. |
| 6,214,332 B1 | 4/2001 | Askill et al. |
| 6,261,276 B1 | 7/2001 | Reitsma |
| 6,345,623 B1 | 2/2002 | Heaton et al. |
| 6,391,294 B1 | 5/2002 | Dettmar et al. |
| 6,398,761 B1 | 6/2002 | Bills et al. |
| 6,447,802 B2 | 9/2002 | Sessions et al. |
| 6,458,109 B1 | 10/2002 | Henley et al. |
| 6,486,285 B2 | 11/2002 | Fujita |
| 6,495,127 B1 | 12/2002 | Wallace et al. |
| 6,509,031 B1 | 1/2003 | Miller et al. |
| 6,521,251 B2 | 2/2003 | Askill et al. |
| 6,527,203 B2 | 3/2003 | Hurray et al. |
| 6,547,467 B2 | 4/2003 | Quintero |
| 6,553,998 B2 | 4/2003 | Heaton et al. |
| 6,564,972 B2 | 5/2003 | Sawhney et al. |
| 6,569,113 B2 | 5/2003 | Wirt et al. |
| 6,575,940 B1 | 6/2003 | Levinson et al. |
| 6,596,704 B1 | 7/2003 | Court et al. |
| 6,626,891 B2 | 9/2003 | Ohmstede |
| 6,627,216 B2 | 9/2003 | Brandt et al. |
| 6,629,774 B1 | 10/2003 | Gruendeman |
| 6,648,852 B2 | 11/2003 | Wirt et al. |
| 6,648,862 B2 | 11/2003 | Watson |
| 6,685,681 B2 | 2/2004 | Lockwood et al. |
| 6,695,823 B1 | 2/2004 | Lina et al. |
| 6,698,622 B2 | 3/2004 | Sawhney et al. |
| 6,730,299 B1 | 5/2004 | Tayot et al. |
| 6,732,887 B2 | 5/2004 | Bills |
| 6,746,428 B2 | 6/2004 | Llorach et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,776,769 B2 | 8/2004 | Smith |
| 6,790,438 B1 | 9/2004 | Constancis et al. |
| 6,800,074 B2 | 10/2004 | Henley et al. |
| 6,814,079 B2 | 11/2004 | Heaton et al. |
| 6,820,766 B2 | 11/2004 | Keller et al. |
| 6,824,533 B2 | 11/2004 | Risk, Jr. et al. |
| 6,840,462 B2 | 1/2005 | Hurray et al. |
| 6,855,135 B2 | 2/2005 | Lockwood et al. |
| 6,856,821 B2 | 2/2005 | Johnson |
| 6,926,695 B2 | 8/2005 | Levinson et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,108,683 B2 | 9/2006 | Zamierowski |
| 7,117,869 B2 | 10/2006 | Heaton et al. |
| 7,128,735 B2 | 10/2006 | Weston |
| 7,129,210 B2 | 10/2006 | Lowinger et al. |
| 7,132,170 B2 | 11/2006 | Parker |
| 7,175,336 B2 | 2/2007 | Voellmicke et al. |
| 7,216,651 B2 | 5/2007 | Argenta et al. |
| 7,303,757 B2 | 12/2007 | Schankereli et al. |
| 7,316,330 B2 | 1/2008 | Muller et al. |
| 7,361,184 B2 | 4/2008 | Joshi |
| 7,381,859 B2 | 6/2008 | Hunt et al. |
| 7,387,432 B2 | 6/2008 | Lu et al. |
| 7,396,507 B2 | 7/2008 | Grunwald et al. |
| 7,524,315 B2 | 4/2009 | Blott et al. |
| 7,534,927 B2 | 5/2009 | Lockwood et al. |
| 7,543,843 B2 | 6/2009 | Keshavaraj et al. |
| 7,569,742 B2 | 8/2009 | Haggstrom et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,635,343 B2 | 12/2009 | McIntosh et al. |
| 7,674,837 B2 | 3/2010 | Gaserod et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,708,940 B2 | 5/2010 | Grunwald et al. |
| 7,717,313 B2 | 5/2010 | Criscuolo et al. |
| 7,718,249 B2 | 5/2010 | Russell et al. |
| 7,722,582 B2 | 5/2010 | Lina et al. |
| 7,723,560 B2 | 5/2010 | Lockwood et al. |

(56) References Cited

U.S. PATENT DOCUMENTS

| | | |
|---|---|---|
| 7,749,531 B2 | 7/2010 | Booher |
| 7,758,554 B2 | 7/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,862,831 B2 | 1/2011 | Wang et al. |
| 7,882,983 B2 | 2/2011 | Reidt et al. |
| 7,910,135 B2 | 3/2011 | St. John et al. |
| 7,910,791 B2 | 3/2011 | Coffey |
| 7,919,182 B2 | 4/2011 | Hamada et al. |
| 7,922,703 B2 | 4/2011 | Riesinger |
| 7,922,743 B2 | 4/2011 | Heinrich et al. |
| 7,927,318 B2 | 4/2011 | Risk, Jr. et al. |
| 7,954,672 B2 | 6/2011 | Keller |
| 7,959,624 B2 | 6/2011 | Riesinger |
| 7,964,766 B2 | 6/2011 | Blott et al. |
| 7,976,519 B2 | 7/2011 | Bubb et al. |
| 8,007,164 B2 | 8/2011 | Miyano et al. |
| 8,025,650 B2 | 9/2011 | Anderson et al. |
| 8,034,037 B2 | 10/2011 | Adams et al. |
| 8,062,272 B2 | 11/2011 | Weston |
| 8,062,331 B2 | 11/2011 | Zamierowski |
| 8,074,843 B2 | 12/2011 | Keller |
| 8,080,702 B2 | 12/2011 | Blott et al. |
| 8,096,979 B2 | 1/2012 | Lina et al. |
| 8,100,887 B2 | 1/2012 | Weston et al. |
| 8,118,794 B2 | 2/2012 | Weston |
| 8,119,160 B2 | 2/2012 | Looney et al. |
| 8,152,785 B2 | 4/2012 | Vitaris |
| 8,162,907 B2 | 4/2012 | Heagle |
| 8,162,909 B2 | 4/2012 | Blott et al. |
| 8,168,848 B2 | 5/2012 | Lockwood et al. |
| 8,192,409 B2 | 6/2012 | Hardman et al. |
| 8,207,392 B2 | 6/2012 | Haggstrom et al. |
| 8,225,981 B2 | 7/2012 | Criscuolo et al. |
| 8,226,942 B2 | 7/2012 | Charier et al. |
| 8,235,972 B2 | 8/2012 | Adahan |
| 8,241,261 B2 | 8/2012 | Randolph et al. |
| 8,267,918 B2 | 9/2012 | Johnson et al. |
| 8,273,368 B2 | 9/2012 | Ambrosio et al. |
| 8,282,611 B2 | 10/2012 | Weston |
| 8,286,832 B2 | 10/2012 | Keller |
| 8,303,552 B2 | 11/2012 | Weston |
| 8,372,049 B2 | 2/2013 | Jaeb et al. |
| 8,372,050 B2 | 2/2013 | Jaeb et al. |
| 8,382,731 B2 | 2/2013 | Johannison |
| 8,410,189 B2 | 4/2013 | Carnahan et al. |
| 8,425,478 B2 | 4/2013 | Olson |
| 8,444,612 B2 | 5/2013 | Patel et al. |
| 8,444,613 B2 | 5/2013 | Svedman et al. |
| 8,454,580 B2 | 6/2013 | Locke et al. |
| 8,460,255 B2 | 6/2013 | Joshi et al. |
| 8,481,801 B2 | 7/2013 | Addison et al. |
| 8,535,296 B2 | 9/2013 | Blott et al. |
| 8,540,688 B2 | 9/2013 | Eckstein et al. |
| 8,540,699 B2 | 9/2013 | Miller et al. |
| 8,545,466 B2 | 10/2013 | Andresen et al. |
| 8,568,386 B2 | 10/2013 | Malhi |
| 8,613,734 B2 | 12/2013 | Lina et al. |
| 8,628,505 B2 | 1/2014 | Weston |
| 8,641,691 B2 | 2/2014 | Fink et al. |
| 8,663,198 B2 | 3/2014 | Buan et al. |
| 8,708,998 B2 | 4/2014 | Weston et al. |
| 8,715,256 B2 | 5/2014 | Greener |
| 8,753,670 B2 | 6/2014 | Delmotte |
| 8,764,732 B2 | 7/2014 | Hartwell |
| 8,791,316 B2 | 7/2014 | Greener |
| 8,795,243 B2 | 8/2014 | Weston |
| 8,795,635 B2 | 8/2014 | Tamarkin et al. |
| 8,795,713 B2 | 8/2014 | Makower et al. |
| 8,795,800 B2 | 8/2014 | Evans |
| 8,801,685 B2 | 8/2014 | Armstrong et al. |
| 8,808,274 B2 | 8/2014 | Hartwell |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,843,327 B2 | 9/2014 | Vernon-Harcourt et al. |
| 8,894,620 B2 | 11/2014 | Swain |
| 8,916,742 B2 | 12/2014 | Smith |
| 8,956,336 B2 | 2/2015 | Haggstrom et al. |
| 8,968,773 B2 | 3/2015 | Thomas et al. |
| 8,998,866 B2 | 4/2015 | Hicks |
| 9,012,714 B2 | 4/2015 | Fleischmann |
| 9,028,872 B2 | 5/2015 | Gaserod et al. |
| 9,067,003 B2 | 6/2015 | Buan et al. |
| 9,173,777 B2 | 11/2015 | Zurovcik |
| 9,199,012 B2 | 12/2015 | Vitaris et al. |
| 9,220,822 B2 | 12/2015 | Hartwell |
| 9,254,353 B2 | 2/2016 | Locke et al. |
| 9,387,126 B2 | 7/2016 | Blott et al. |
| 9,421,309 B2 | 8/2016 | Robinson et al. |
| 9,446,178 B2 | 9/2016 | Blott et al. |
| 9,492,326 B2 | 11/2016 | Miller et al. |
| 9,629,986 B2 | 4/2017 | Patel et al. |
| 9,682,179 B2 | 6/2017 | May |
| 2001/0004082 A1 | 6/2001 | Keller et al. |
| 2001/0043913 A1 | 11/2001 | Spaans et al. |
| 2002/0010299 A1 | 1/2002 | Guyuron et al. |
| 2002/0038826 A1 | 4/2002 | Hurray et al. |
| 2002/0122771 A1 | 9/2002 | Holland et al. |
| 2002/0143286 A1 | 10/2002 | Tumey |
| 2002/0145007 A1 | 10/2002 | Sawhney et al. |
| 2002/0146662 A1 | 10/2002 | Radl et al. |
| 2002/0183702 A1 | 12/2002 | Henley et al. |
| 2002/0187182 A1 | 12/2002 | Kramer et al. |
| 2002/0198490 A1 | 12/2002 | Wirt et al. |
| 2003/0040478 A1 | 2/2003 | Drucker et al. |
| 2003/0069535 A1 | 4/2003 | Shalaby |
| 2003/0069563 A1 | 4/2003 | Johnson |
| 2003/0093041 A1 | 5/2003 | Risk, Jr. et al. |
| 2003/0125646 A1 | 7/2003 | Whitlock |
| 2003/0143189 A1 | 7/2003 | Askill et al. |
| 2003/0183653 A1 | 10/2003 | Bills |
| 2003/0212357 A1 | 11/2003 | Pace |
| 2004/0033466 A1 | 2/2004 | Shellard et al. |
| 2004/0037897 A1 | 2/2004 | Benjamin et al. |
| 2004/0049187 A1 | 3/2004 | Burnett et al. |
| 2004/0057855 A1 | 3/2004 | Gerlach et al. |
| 2004/0073152 A1 | 4/2004 | Karason et al. |
| 2004/0084812 A1 | 5/2004 | Grunwald et al. |
| 2004/0121438 A1 | 6/2004 | Quirk |
| 2004/0167617 A1 | 8/2004 | Voellmicke et al. |
| 2004/0171998 A1 | 9/2004 | Marasco, Jr. |
| 2005/0020955 A1 | 1/2005 | Sanders et al. |
| 2005/0085795 A1 | 4/2005 | Lockwood et al. |
| 2005/0100692 A1 | 5/2005 | Parker |
| 2005/0137272 A1 | 6/2005 | Gaserod et al. |
| 2005/0163904 A1 | 7/2005 | Walker et al. |
| 2005/0230422 A1 | 10/2005 | Muller et al. |
| 2006/0009577 A1 | 1/2006 | Hara |
| 2006/0009744 A1 | 1/2006 | Erdman et al. |
| 2006/0079599 A1 | 4/2006 | Arthur |
| 2006/0100586 A1 | 5/2006 | Karpowicz et al. |
| 2006/0173253 A1 | 8/2006 | Ganapathy et al. |
| 2006/0173514 A1 | 8/2006 | Biel et al. |
| 2006/0217016 A1 | 9/2006 | Lin et al. |
| 2006/0228318 A1 | 10/2006 | Fabo |
| 2006/0253082 A1 | 11/2006 | McIntosh et al. |
| 2006/0273109 A1 | 12/2006 | Keller |
| 2007/0004896 A1 | 1/2007 | Ito et al. |
| 2007/0009580 A1 | 1/2007 | DiCosmo et al. |
| 2007/0040454 A1 | 2/2007 | Freudenberger et al. |
| 2007/0055209 A1 | 3/2007 | Patel et al. |
| 2007/0141101 A1 | 6/2007 | Nugent et al. |
| 2007/0147947 A1 | 6/2007 | Stenton et al. |
| 2007/0164047 A1 | 7/2007 | Reidt et al. |
| 2007/0185463 A1 | 8/2007 | Mulligan |
| 2007/0186404 A1 | 8/2007 | Drew et al. |
| 2007/0203062 A1 | 8/2007 | Ellis-Behnke et al. |

(56) References Cited

U.S. PATENT DOCUMENTS

| | | |
|---|---|---|
| 2007/0219513 A1 | 9/2007 | Lina et al. |
| 2007/0225663 A1 | 9/2007 | Watt et al. |
| 2007/0237811 A1 | 10/2007 | Scherr |
| 2007/0248642 A1 | 10/2007 | Dornish et al. |
| 2008/0004549 A1 | 1/2008 | Anderson et al. |
| 2008/0031748 A1 | 2/2008 | Ihle et al. |
| 2008/0060550 A1 | 3/2008 | MacDonald et al. |
| 2008/0089173 A1 | 4/2008 | Lu et al. |
| 2008/0132821 A1 | 6/2008 | Propp et al. |
| 2008/0206155 A1 | 8/2008 | Tamarkin et al. |
| 2008/0208163 A1 | 8/2008 | Wilkie |
| 2008/0232187 A1 | 9/2008 | Miyano et al. |
| 2008/0249259 A1 | 10/2008 | Kashiwagi |
| 2008/0254103 A1 | 10/2008 | Harris et al. |
| 2008/0279807 A1 | 11/2008 | Belcheva et al. |
| 2008/0287880 A1 | 11/2008 | Keller |
| 2008/0306456 A1 | 12/2008 | Riesinger |
| 2008/0314929 A1 | 12/2008 | Keller |
| 2009/0020561 A1 | 1/2009 | Keller |
| 2009/0022779 A1 | 1/2009 | Kelly et al. |
| 2009/0030086 A1 | 1/2009 | Eady et al. |
| 2009/0093550 A1 | 4/2009 | Rolfes et al. |
| 2009/0098073 A1 | 4/2009 | MacDonald et al. |
| 2009/0098503 A1 | 4/2009 | Knispel et al. |
| 2009/0125004 A1 | 5/2009 | Shen et al. |
| 2009/0134186 A1 | 5/2009 | Keller |
| 2009/0157017 A1 | 6/2009 | Ambrosio |
| 2009/0157024 A1 | 6/2009 | Song |
| 2009/0196844 A1 | 8/2009 | Choi et al. |
| 2009/0234306 A1 | 9/2009 | Vitaris |
| 2009/0254053 A1 | 10/2009 | Svensby et al. |
| 2009/0275872 A1 | 11/2009 | Addison et al. |
| 2009/0299251 A1 | 12/2009 | Buan |
| 2009/0299255 A1 | 12/2009 | Kazala, Jr. et al. |
| 2009/0299306 A1 | 12/2009 | Buan |
| 2010/0012210 A1 | 1/2010 | Miyano et al. |
| 2010/0022972 A1 | 1/2010 | Lina et al. |
| 2010/0030132 A1 | 2/2010 | Niezgoda et al. |
| 2010/0036305 A1 | 2/2010 | Green |
| 2010/0036334 A1 | 2/2010 | Heagle et al. |
| 2010/0069850 A1 | 3/2010 | Fabo |
| 2010/0125258 A1 | 5/2010 | Coulthard et al. |
| 2010/0125259 A1 | 5/2010 | Olson |
| 2010/0135915 A1 | 6/2010 | Greener |
| 2010/0137775 A1 | 6/2010 | Hu et al. |
| 2010/0230467 A1 | 9/2010 | Criscuolo et al. |
| 2010/0259406 A1 | 10/2010 | Caso et al. |
| 2010/0268177 A1 | 10/2010 | Hall et al. |
| 2010/0318052 A1 | 12/2010 | Ha et al. |
| 2011/0004172 A1 | 1/2011 | Eckstein et al. |
| 2011/0021431 A1 | 1/2011 | Jones et al. |
| 2011/0028919 A1 | 2/2011 | Johnnison et al. |
| 2011/0033503 A1 | 2/2011 | Sinko et al. |
| 2011/0036889 A1 | 2/2011 | Heinrich et al. |
| 2011/0066123 A1 | 3/2011 | Tout et al. |
| 2011/0086077 A1 | 4/2011 | McCrea et al. |
| 2011/0118683 A1 | 5/2011 | Weston |
| 2011/0144599 A1 | 6/2011 | Croizat et al. |
| 2011/0147432 A1 | 6/2011 | Heinrich et al. |
| 2011/0147435 A1 | 6/2011 | Heinrich et al. |
| 2011/0224631 A1 | 9/2011 | Simmons et al. |
| 2011/0250447 A1 | 10/2011 | Taniguchi et al. |
| 2011/0257611 A1 | 10/2011 | Locke et al. |
| 2011/0313374 A1 | 12/2011 | Lockwood et al. |
| 2012/0051945 A1 | 3/2012 | Orndorff et al. |
| 2012/0083755 A1 | 4/2012 | Lina et al. |
| 2012/0095380 A1 | 4/2012 | Gergely et al. |
| 2012/0123356 A1 | 5/2012 | Greener |
| 2012/0123358 A1 | 5/2012 | Hall et al. |
| 2012/0222687 A1 | 9/2012 | Czajka, Jr. et al. |
| 2013/0023841 A1 | 1/2013 | Johnson et al. |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0138054 A1 | 5/2013 | Fleischmann |
| 2013/0144227 A1 | 6/2013 | Locke et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0274688 A1 | 10/2013 | Weston |
| 2013/0296762 A1 | 11/2013 | Toth |
| 2013/0302545 A1 | 11/2013 | Schnelker et al. |
| 2014/0114268 A1 | 4/2014 | Auguste et al. |
| 2014/0171888 A1 | 6/2014 | Croizat et al. |
| 2014/0228791 A1 | 8/2014 | Hartwell |
| 2014/0228792 A1 | 8/2014 | Weston et al. |
| 2014/0316359 A1 | 10/2014 | Collinson et al. |
| 2015/0159066 A1 | 6/2015 | Hartwell et al. |
| 2015/0190286 A1 | 7/2015 | Allen et al. |
| 2015/0216733 A1 | 8/2015 | Allen et al. |
| 2015/0320604 A1 | 11/2015 | Adie et al. |
| 2016/0074232 A1 | 3/2016 | Vitaris et al. |
| 2016/0120706 A1 | 5/2016 | Collinson et al. |
| 2016/0144084 A1 | 5/2016 | Collinson et al. |

FOREIGN PATENT DOCUMENTS

| | | |
|---|---|---|
| DE | 3838587 A1 | 5/1990 |
| DE | 202004017052 U1 | 6/2005 |
| EP | 0251810 A2 | 1/1988 |
| EP | 0340018 A2 | 11/1989 |
| EP | 0358302 A2 | 3/1990 |
| EP | 0425164 A1 | 5/1991 |
| EP | 0322118 B1 | 6/1992 |
| EP | 0521434 A1 | 1/1993 |
| EP | 0325771 B1 | 9/1993 |
| EP | 0617152 A1 | 9/1994 |
| EP | 0578999 B1 | 5/1996 |
| EP | 0549781 B1 | 9/1996 |
| EP | 0762860 A1 | 3/1997 |
| EP | 0506241 B1 | 5/1997 |
| EP | 0793019 A2 | 9/1997 |
| EP | 0620720 B1 | 3/1998 |
| EP | 0858810 A2 | 8/1998 |
| EP | 0651983 B1 | 9/1998 |
| EP | 0888141 A1 | 1/1999 |
| EP | 0912251 A1 | 5/1999 |
| EP | 0923905 A2 | 6/1999 |
| EP | 1007015 A1 | 6/2000 |
| EP | 1013290 A1 | 6/2000 |
| EP | 1029585 A1 | 8/2000 |
| EP | 0688189 B1 | 9/2000 |
| EP | 1088569 A2 | 4/2001 |
| EP | 1105171 A2 | 6/2001 |
| EP | 1105180 A1 | 6/2001 |
| EP | 1107813 A1 | 6/2001 |
| EP | 1114933 A2 | 7/2001 |
| EP | 1030657 B1 | 10/2001 |
| EP | 1139951 A2 | 10/2001 |
| EP | 0921775 B1 | 12/2001 |
| EP | 1177781 A2 | 2/2002 |
| EP | 1306123 A1 | 5/2003 |
| EP | 1440737 A1 | 7/2004 |
| EP | 1018967 B1 | 8/2004 |
| EP | 1633830 A2 | 3/2006 |
| EP | 1637088 A2 | 3/2006 |
| EP | 1798835 A1 | 6/2007 |
| EP | 1476217 B1 | 3/2008 |
| EP | 1955887 A2 | 8/2008 |
| EP | 1978046 A2 | 10/2008 |
| EP | 1988125 A2 | 11/2008 |
| EP | 2111804 A2 | 10/2009 |
| EP | 2127690 A2 | 12/2009 |
| EP | 2263627 A2 | 12/2010 |
| EP | 1374914 B1 | 3/2011 |
| EP | 2335747 A1 | 6/2011 |
| EP | 2366721 A1 | 9/2011 |
| EP | 2462908 A1 | 6/2012 |
| EP | 2529767 A2 | 12/2012 |
| EP | 2477674 B1 | 7/2013 |
| EP | 2544642 B1 | 1/2015 |
| EP | 2648668 A4 | 1/2015 |
| FR | 1163907 A | 10/1958 |
| GB | 1255395 A | 12/1971 |

(56) References Cited

FOREIGN PATENT DOCUMENTS

| | | | |
|---|---|---|---|
| GB | 2288734 A | 11/1995 |
| GB | 2306580 A | 5/1997 |
| GB | 2329127 A | 3/1999 |
| GB | 2305610 B | 7/1999 |
| GB | 2389794 A | 12/2003 |
| GB | 2423019 A | 8/2006 |
| GB | 2424582 A | 10/2006 |
| GB | 2435422 A | 8/2007 |
| GB | 2435419 B | 3/2008 |
| GB | 2468905 A | 9/2010 |
| JP | S5936608 A | 2/1984 |
| JP | H0570692 A | 3/1993 |
| JP | 2005261376 A | 9/2005 |
| JP | 2005334188 A | 12/2005 |
| JP | 2009148393 A | 7/2009 |
| WO | WO-8300742 A1 | 3/1983 |
| WO | WO-9209301 A1 | 6/1992 |
| WO | WO-9209651 A1 | 6/1992 |
| WO | WO-9210983 A1 | 7/1992 |
| WO | WO-9216245 A1 | 10/1992 |
| WO | WO-9306802 A1 | 4/1993 |
| WO | WO-9309176 A2 | 5/1993 |
| WO | WO-9309727 A1 | 5/1993 |
| WO | WO-9420133 A1 | 9/1994 |
| WO | WO-9421207 A2 | 9/1994 |
| WO | WO-9504511 A1 | 2/1995 |
| WO | WO-9529959 A1 | 11/1995 |
| WO | WO-9601731 A1 | 1/1996 |
| WO | WO-9605873 A1 | 2/1996 |
| WO | WO-9640174 A1 | 12/1996 |
| WO | WO-9703717 A1 | 2/1997 |
| WO | WO-9711658 A1 | 4/1997 |
| WO | WO-9714384 A1 | 4/1997 |
| WO | WO-9733922 A1 | 9/1997 |
| WO | WO-9738732 A2 | 10/1997 |
| WO | WO-9742986 A1 | 11/1997 |
| WO | WO-9743991 A1 | 11/1997 |
| WO | WO-9803267 A1 | 1/1998 |
| WO | WO-9806444 A1 | 2/1998 |
| WO | WO-9813000 A1 | 4/1998 |
| WO | WO-9917698 A1 | 4/1999 |
| WO | WO-9919013 A1 | 4/1999 |
| WO | WO-9930629 A1 | 6/1999 |
| WO | WO-9939671 A1 | 8/1999 |
| WO | WO-9947097 A2 | 9/1999 |
| WO | WO-9948621 A2 | 9/1999 |
| WO | WO-9965536 A1 | 12/1999 |
| WO | WO-0000016 A1 | 1/2000 |
| WO | WO-0017968 A1 | 3/2000 |
| WO | WO-0038752 A1 | 7/2000 |
| WO | WO-0040190 A1 | 7/2000 |
| WO | WO-0061206 A1 | 10/2000 |
| WO | WO-0062827 A2 | 10/2000 |
| WO | WO-0064394 A1 | 11/2000 |
| WO | WO-0064396 A1 | 11/2000 |
| WO | WO-0074738 A1 | 12/2000 |
| WO | WO-0110363 A1 | 2/2001 |
| WO | WO-0137773 A1 | 5/2001 |
| WO | WO-0149233 A1 | 7/2001 |
| WO | WO-0162312 A1 | 8/2001 |
| WO | WO-0166017 A1 | 9/2001 |
| WO | WO-0172251 A1 | 10/2001 |
| WO | WO-0187271 A1 | 11/2001 |
| WO | WO-0189588 A1 | 11/2001 |
| WO | WO-0202079 A1 | 1/2002 |
| WO | WO-0205737 A1 | 1/2002 |
| WO | WO-0217840 A1 | 3/2002 |
| WO | WO-0224132 A2 | 3/2002 |
| WO | WO-0238096 A2 | 5/2002 |
| WO | WO-02070040 A1 | 9/2002 |
| WO | WO-02094256 A1 | 11/2002 |
| WO | WO-02102864 A1 | 12/2002 |
| WO | WO-03005943 A2 | 1/2003 |
| WO | WO-03022333 A1 | 3/2003 |
| WO | WO-03041786 A1 | 5/2003 |
| WO | WO-03065877 A2 | 8/2003 |
| WO | WO-03072748 A2 | 9/2003 |
| WO | WO-2004016313 A1 | 2/2004 |
| WO | WO-2004037334 A1 | 5/2004 |
| WO | WO-2004052982 A2 | 6/2004 |
| WO | WO-2004054632 A1 | 7/2004 |
| WO | WO-2004060148 A2 | 7/2004 |
| WO | WO-2004077387 A1 | 9/2004 |
| WO | WO-2004098474 A1 | 11/2004 |
| WO | WO-2004108175 A1 | 12/2004 |
| WO | WO-2005009488 A2 | 2/2005 |
| WO | WO-2005017000 A1 | 2/2005 |
| WO | WO-2005018695 A1 | 3/2005 |
| WO | WO-2005019343 A1 | 3/2005 |
| WO | WO-2005025447 A2 | 3/2005 |
| WO | WO-2005046760 A1 | 5/2005 |
| WO | WO-2005082435 A1 | 9/2005 |
| WO | WO-2005105180 A1 | 11/2005 |
| WO | WO-2005118011 A1 | 12/2005 |
| WO | WO-2005123170 A1 | 12/2005 |
| WO | WO-2006005939 A1 | 1/2006 |
| WO | WO-2006014534 A2 | 2/2006 |
| WO | WO-2006028244 A1 | 3/2006 |
| WO | WO-2006030054 A1 | 3/2006 |
| WO | WO-2006034128 A2 | 3/2006 |
| WO | WO-2006034166 A2 | 3/2006 |
| WO | WO-2006046060 A2 | 5/2006 |
| WO | WO-2006052839 A2 | 5/2006 |
| WO | WO-2006081403 A1 | 8/2006 |
| WO | WO-2006114637 A2 | 11/2006 |
| WO | WO-2006116992 A1 | 11/2006 |
| WO | WO-2006135506 A2 | 12/2006 |
| WO | WO-2006135934 A2 | 12/2006 |
| WO | WO-2007031757 A2 | 3/2007 |
| WO | WO-2007031762 A1 | 3/2007 |
| WO | WO-2007092397 A2 | 8/2007 |
| WO | WO-2007095180 A2 | 8/2007 |
| WO | WO-2007106590 A2 | 9/2007 |
| WO | WO-2007106594 A2 | 9/2007 |
| WO | WO-2007113597 A2 | 10/2007 |
| WO | WO-2007116347 A2 | 10/2007 |
| WO | WO-2007123451 A1 | 11/2007 |
| WO | WO-2007124198 A2 | 11/2007 |
| WO | WO-2007133618 A2 | 11/2007 |
| WO | WO-2007143060 A2 | 12/2007 |
| WO | WO-2008008032 A1 | 1/2008 |
| WO | WO-2008028494 A2 | 3/2008 |
| WO | WO-2008036162 A2 | 3/2008 |
| WO | WO-2008039223 A1 | 4/2008 |
| WO | WO-2008040681 A1 | 4/2008 |
| WO | WO-2008043067 A2 | 4/2008 |
| WO | WO-2008060475 A2 | 5/2008 |
| WO | WO-2008076407 A2 | 6/2008 |
| WO | WO-2008082444 A2 | 7/2008 |
| WO | WO-2008086397 A2 | 7/2008 |
| WO | WO-2008100437 A1 | 8/2008 |
| WO | WO-2008104609 A1 | 9/2008 |
| WO | WO-2008134544 A1 | 11/2008 |
| WO | WO-2008134774 A2 | 11/2008 |
| WO | WO-2008135997 A2 | 11/2008 |
| WO | WO-2009011856 A1 | 1/2009 |
| WO | WO-2009042514 A1 | 4/2009 |
| WO | WO-2009047524 A2 | 4/2009 |
| WO | WO-2009052193 A1 | 4/2009 |
| WO | WO-2009060327 A2 | 5/2009 |
| WO | WO-2009062327 A1 | 5/2009 |
| WO | WO-2009077722 A1 | 6/2009 |
| WO | WO-2009086580 A1 | 7/2009 |
| WO | WO-2009088925 A1 | 7/2009 |
| WO | WO-2009090074 A1 | 7/2009 |
| WO | WO-2009102021 A1 | 8/2009 |
| WO | WO-2009103031 A1 | 8/2009 |
| WO | WO-2009122989 A1 | 10/2009 |
| WO | WO-2009124100 A1 | 10/2009 |
| WO | WO-2009124407 A1 | 10/2009 |
| WO | WO-2009126102 A1 | 10/2009 |
| WO | WO-2009146441 A1 | 12/2009 |
| WO | WO-2009147402 A2 | 12/2009 |
| WO | WO-2009156709 A1 | 12/2009 |

(56) References Cited

FOREIGN PATENT DOCUMENTS

| WO | WO-2009158128 A2 | 12/2009 |
| WO | WO-2010006182 A2 | 1/2010 |
| WO | WO-2010019997 A1 | 2/2010 |
| WO | WO-2010121033 A2 | 10/2010 |
| WO | WO-2010122665 A1 | 10/2010 |
| WO | WO-2010142959 A2 | 12/2010 |
| WO | WO-2010147533 A1 | 12/2010 |
| WO | WO-2011072840 A1 | 6/2011 |
| WO | WO-2011112870 A1 | 9/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2012009370 A2 | 1/2012 |
| WO | WO-2012021553 A1 | 2/2012 |
| WO | WO-2012041296 A2 | 4/2012 |
| WO | WO-2012069793 A1 | 5/2012 |
| WO | WO-2012069794 A1 | 5/2012 |
| WO | WO-2012074512 A1 | 6/2012 |
| WO | WO-2012078707 A1 | 6/2012 |
| WO | WO-2012131237 A1 | 10/2012 |
| WO | WO-2012140378 A1 | 10/2012 |
| WO | WO-2012143665 A1 | 10/2012 |
| WO | WO-2013010907 A1 | 1/2013 |
| WO | WO-2013029652 A1 | 3/2013 |
| WO | WO-2013033131 A1 | 3/2013 |
| WO | WO-2013064852 A1 | 5/2013 |
| WO | WO-2013076450 A1 | 5/2013 |
| WO | WO-2013083800 A1 | 6/2013 |
| WO | WO-2013110008 A1 | 7/2013 |
| WO | WO-2013136181 A2 | 9/2013 |
| WO | WO-2013149078 A1 | 10/2013 |
| WO | WO-2014008348 A2 | 1/2014 |
| WO | WO-2014020440 A1 | 2/2014 |
| WO | WO-2014020443 A2 | 2/2014 |
| WO | WO-2014108476 A1 | 7/2014 |
| WO | WO-2014113253 A1 | 7/2014 |
| WO | WO-2015022334 A1 | 2/2015 |

OTHER PUBLICATIONS

Dethier P., et al., "X-ray Sterilisation," The Technology of the Future, retrieved from http://www.emdt.co.uk/article/x-ray-sterilisation-technology-future, Feb. 1, 2010, 3 pages.

Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.

Huang H.S., Beijing: Quality Management in Drug Production, China Medical Science Press, Feb. 28, 2009, pp. 65-66.

International Preliminary Report on Patentability for Application No. PCT/GB2011/001649, dated Jun. 6, 2013.

International Preliminary Report on Patentability for Application No. PCT/GB2011/001652, dated Mar. 18, 2013, 23 pages.

International Search Report for Application No. PCT/GB2011/001649, dated Mar. 6, 2012, 4 pages.

International Search Report on Patentability for Application No. PCT/GB2011/001652, dated May 18, 2012, 6 pages.

Jahns B., et al., "Problem Wound Therapy with a New Mouldable Silicone Foam Dressing Using The Vaccum Technique," 2nd Congress of German Wound Therapy Society, 1998, 5 pages.

Kendall ULTEC Hydrocolloid Dressing (4x4"), Product Ordering Page, web page downloaded on Jul. 13, 2014, 1 page.

Khan T.A., et al., "Influence of Chitosan Molecular Weight on its Physical Properties," EIMJM, vol. 2(1), 2003, pp. 1-8.

Letter/Objections from Dr. Tanja Bendele, LLM at RUHR for the European Patent No. 2643412, dated Apr. 1, 2015, 8 pages.

Letter/Observations from Dr. Tanja Bendele, LLM at RUHR EP2643027, dated May 29, 2015, 10 pages.

Letter/Opposition from Dr. Tanja Bendele, LLM at RUHR for the European Patent No. 2643027, dated May 21, 2014, 17 pages.

Meissner J., "X-ray Sterilisation," Published Mar. 1, 2008, retrieved from http://www.emdt.co.uk/article/x-ray-sterilisation, 3 pages.

Product Data Sheet, Wacker SiiGel 612 A/B, Jun. 2014, 3 pages.

Protz K., "Modern Wound Dressings Support the Healing Process," Wound care: Indications and Application, Geriatrie Journal, Apr. 2005, pp. 3333-3339 (17 pages with English translation).

Smith & Nephew, "PICO Single Use Negative Pressure Wound Therapy System," Spiral Booklet, Mar. 2011, 7 pages.

Sogias I.A., et al., "Exploring the Factors Affecting the Solubility of Chitosan in Water," Macromolecular Chemistry and Physics, vol. 211, 2010, pp. 426-433.

Technology Watch, May 1989, 1 page.

Wacker, "Silpuran® 2445 A/B," Technical Datasheet, Version 1.7, Oct. 11, 2014, 3 pages.

Wooding-Scott M., et al., "No Wound is Too Big for Resourceful Nurses," RN, Dec. 1988, pp. 22-25.

Cheng Bu., et al., "Collection of Golden Ideas for Home," Qingdao Publishing House, First Edition, Mar. 2011, p. 432.

* cited by examiner

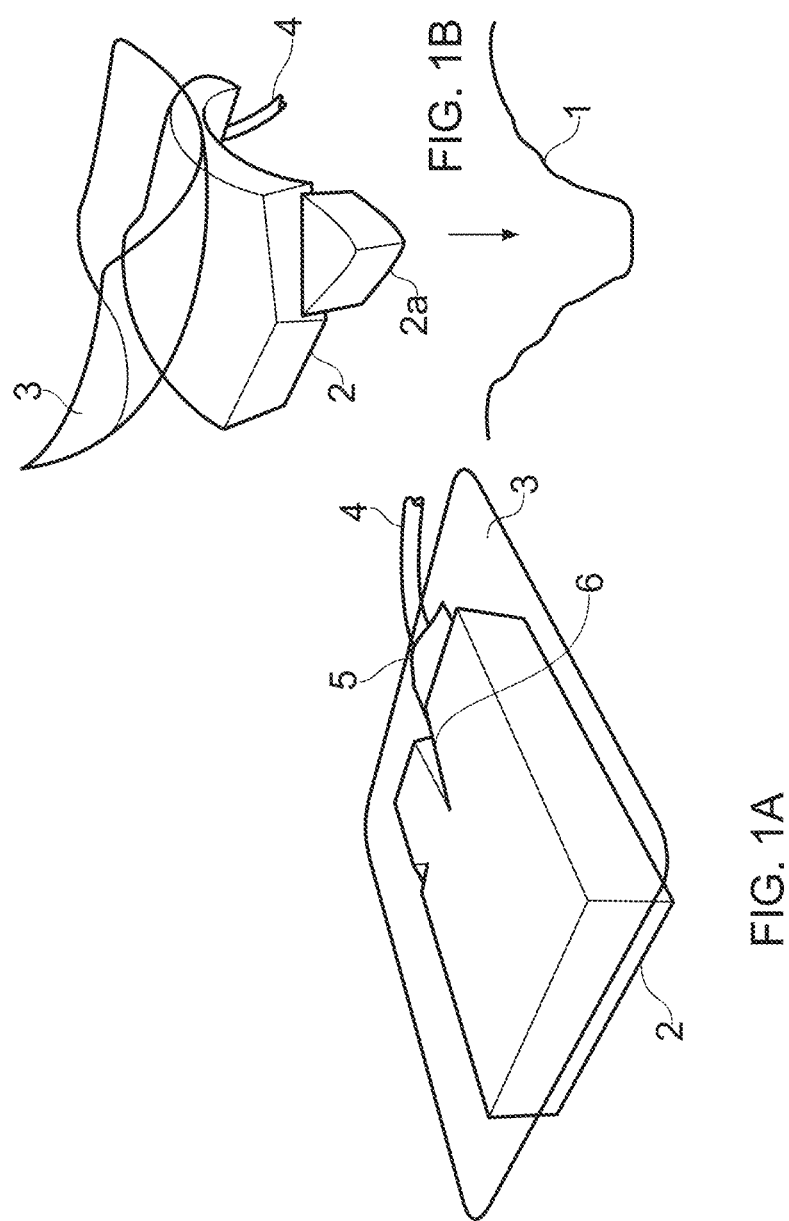

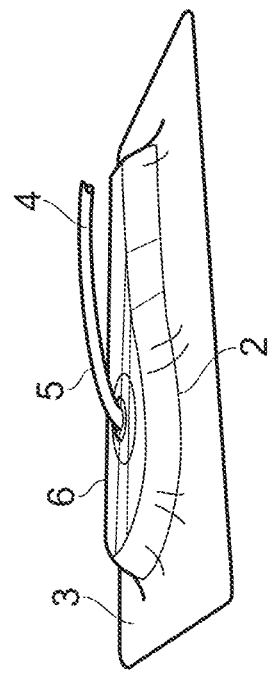
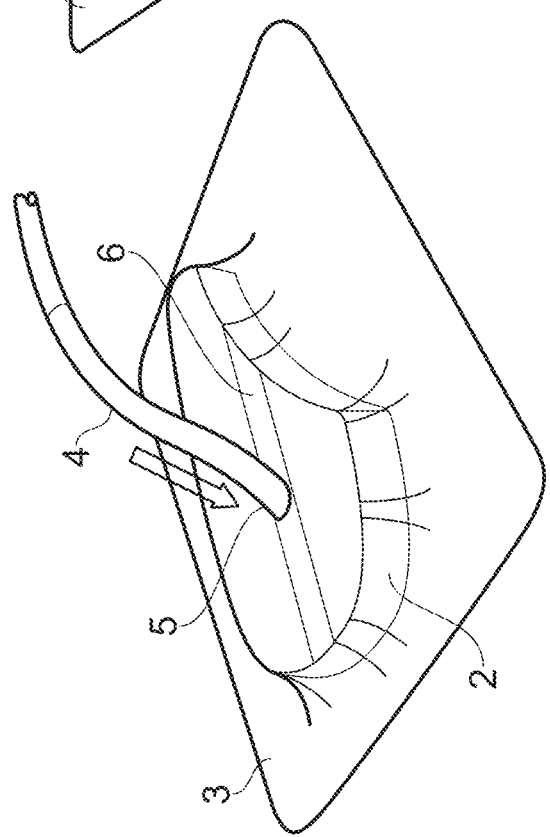

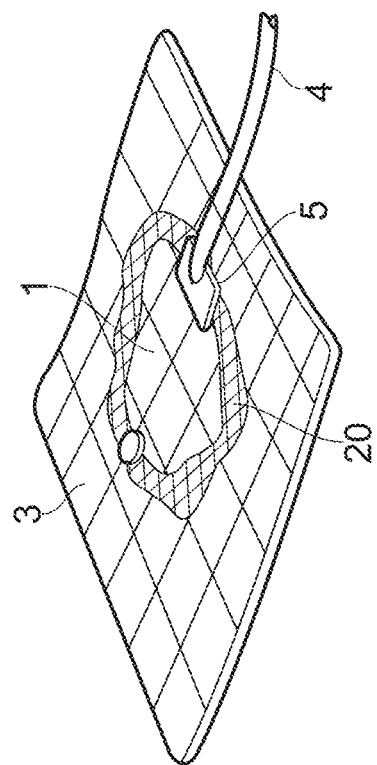
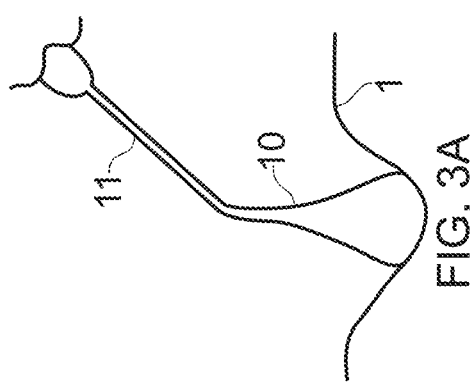
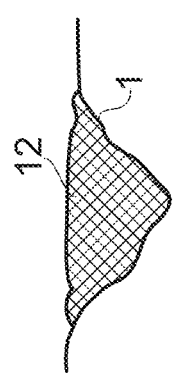
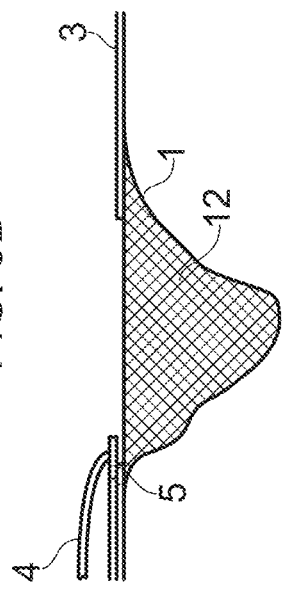

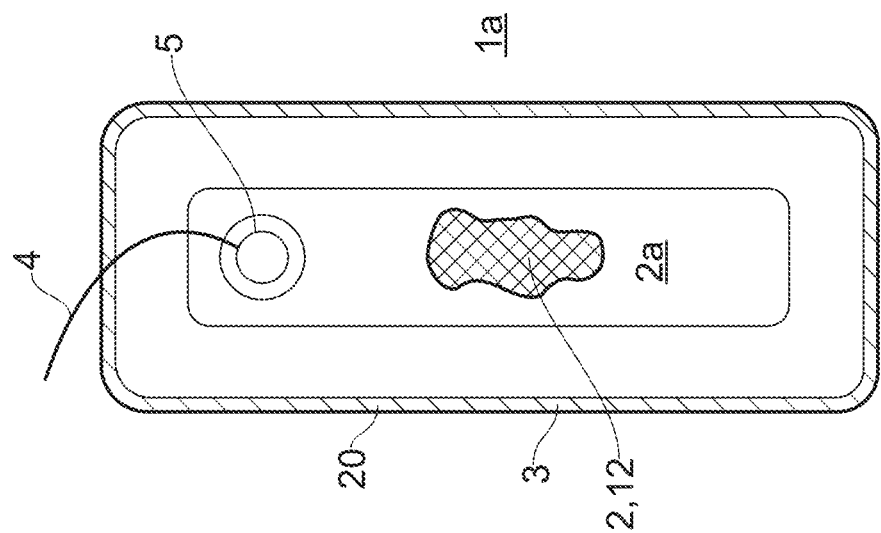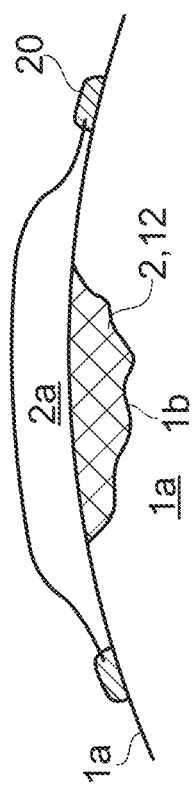
FIG. 11A
FIG. 11B

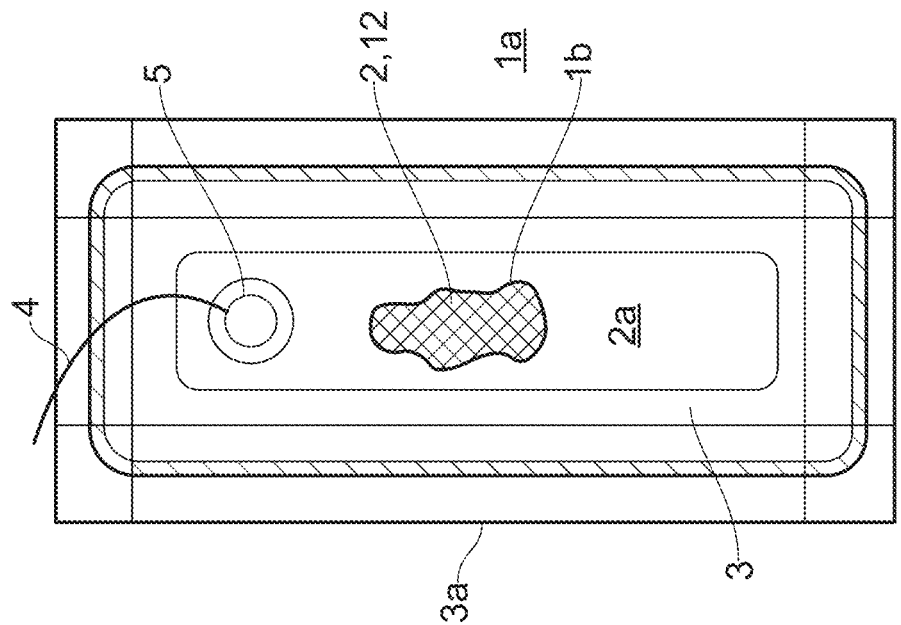
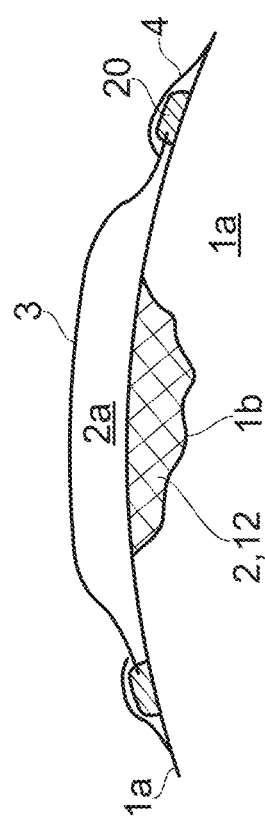
FIG. 12B
FIG. 12A

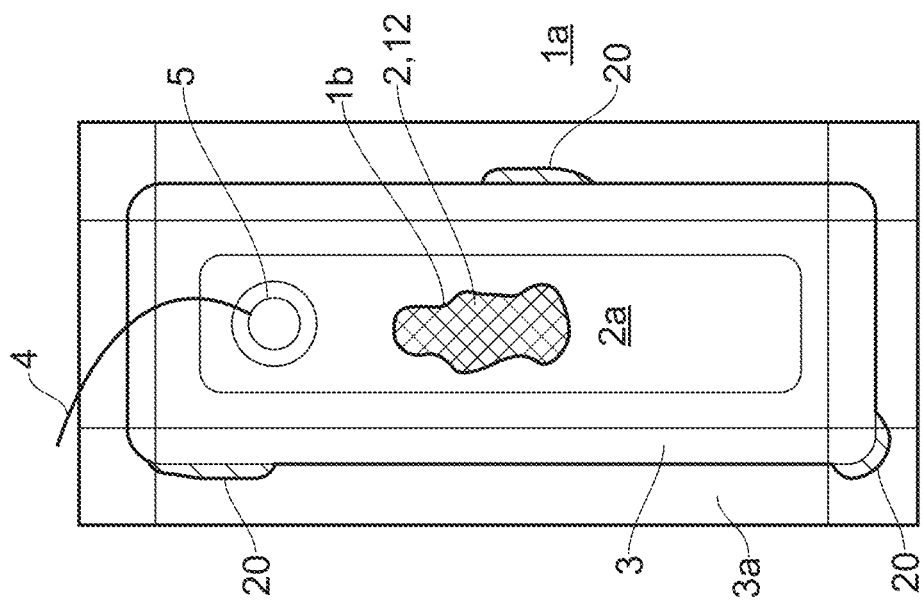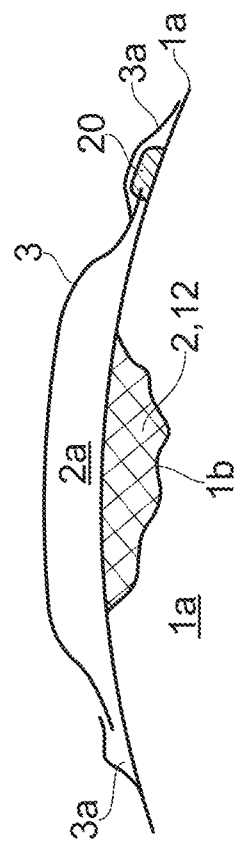
FIG. 14B
FIG. 14A

COMPOSITIONS I-I AND PRODUCTS AND USES THEREOF

CROSS-REFERENCE TO RELATED APPLICATIONS

This application is a divisional application of U.S. application Ser. No. 16/213,630, filed on Dec. 7, 2018, which is a continuation of abandoned U.S. application Ser. No. 13/989,560, filed on Aug. 8, 2013, which is a U.S. National Phase application under 35 U.S.C. § 371 of International Application PCT/GB2011/001649, filed Nov. 25, 2011, which claims priority to Great Britain Patent Application No. 1020005.3, filed Nov. 25, 2010.

BACKGROUND

Field

Embodiments of the present invention relate to a two part, curable composition, methods for preparing the composition, manufacture thereof and methods for sterilisation thereof, medical and non-medical use thereof, methods for use or therapy therewith, a device incorporating the composition, and a precursor therefor including its sterilisable precursor composition. In particular, certain embodiments of the invention relates to a sterilisable or sterile composition for medical use, particularly in wound therapy, more particularly as a wound packing material or filler which can be shaped and configured to the shape of a wound, or an adhesive or sealant for a wound dressing, most particularly for application in negative pressure wound therapy (NPWT).

Description of the Related Art

NPWT is a relatively new treatment for open wounds. Briefly, negative pressure therapy can assist in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilise the tissue in the apposed position of closure. A further beneficial use of TNP therapy can be found in grafts and flaps where removal of excess fluid is important and close proximity of the graft to tissue is required in order to ensure tissue viability. Typically in NPWT the wound cavity or surface is filled or covered with a material that allows the transmission of a partial vacuum (i.e. does not completely collapse) to the wound bed when a negative pressure is applied to the wound area, and also allows fluids to pass from the wound bed towards the source of negative pressure. There are two primary approaches to NPWT, i.e. gauze or foam types. The gauze type involves the use of a drain wrapped in gauze topped by a sealed dressing. The foam type involves the use of foam placed over or in the wound, also topped by a sealed dressing. One embodiment is directed primarily towards the foam type of NPWT. Further embodiments are directed towards either the foam or gauze type of NPWT, or to a further type of NPWT which uses a sealed dressing as a combination or preformed with additional absorption or distribution layers or the like.

A good material for the foam based NPWT application which offers good resistance to compression under loading, is hydrophobic, reticulated polyurethane foam of high free internal volume.

However articles of high free internal volume tend to be poorly drapeable due to the requirement for their structure to mechanically support their high free internal volume, and this is the case in foams applied in NPWT.

Therefore packing material for use in NPWT must be shaped to fit the wound to be packed. This is typically achieved by the medical practitioner (physician or nurse) cutting a preformed block of foam to approximately fit the wound using a scalpel, knife or scissors. This operation can be complex and has the potential to introduce contamination, moreover is time consuming and messy for the medical practitioner, and indeed can be dangerous with the possibility of particulate foam contaminating the wound site or of an accident during the cutting process. Accordingly the process of shaping the wound dressing is currently an unaddressed problem in the field of NPWT.

Castable compositions are known for use in wound care. WO2009/156709 discloses a topical negative pressure, or vacuum, wound therapy wound covering element or drape constructed of silicone or polyurethane based materials, which provides a substantially air-tight seal over a wound, having a vacuum connection tube or line for connection to a negative pressure source moulded or glued in place to reduce the likelihood of negative pressure leakage. The drape may be manufactured by casting a two-part heat curable silicone elastomer over the vacuum line, located in a mould. The resulting drape may be sterilised by irradiation and packaged in sterile form until required for use by placing over a foam or gauze wound filler.

An RTV-2 (addition cure two-part room temperature vulcanizing) silicone foam wound dressing, Cavi-Care, is sold non-sterile. U.S. Pat. No. 5,153,231 discloses the composition which is capable of providing a low density foamed medical dressing by releasing two components into a mixing vessel by rupture of their individual packaging, mixing and dispensing or casting onto a surface such as an open wound and allowing the mixture to cure at room temperature.

It would be useful to provide a castable in-situ wound filler in the form of an RTV-2 silicone foam. It would also be useful to provide a castable in-situ adhesive or sealant for a NPWT drape or dressing. The problem is that for an RTV-2 wound filler, adhesive, sealant or the like to be viable the two part system must be available sterile.

Where a product for medical use is required to be sterile at point of use, it is a well accepted principle that it should be manufactured using aseptic processing only when terminal sterilisation is not feasible. To ensure the highest levels of sterility assurance for a medical product, it should therefore be terminally sterilised in its final packaging.

Although sterile foamed wound dressing materials are available such as Allevyn™, a polyurethane foam wound covering element, and black foam ("Granufoam"), a polyurethane wound filler, supplied packaged in a peel pouch, no two-part RTV-2 silicone composition or indeed any RTV-2 composition, foamable or otherwise, appears to be available sterile, as the two part system prior to curing, either terminally sterilised in primary packaging or sterilised and then aseptically packaged. Furthermore a process for sterilising these systems does not appear to be available.

One object of the invention is to provide an improved terminally sterile RTV-2 foamable silicone composition. It is a further object to provide an improved, terminally sterile, wound filler which can be conformed to the shape of a wound cavity. It is a further object to provide a terminally sterile RTV-2 non-foamable or partially foamable silicone composition. It is a further object to provide a terminally sterile adhesive or sealant which can be conformed about a wound cavity.

In attempting to find a route to sterilise a two part foamable curable silicone composition which could be cast into a desired shape and cured in situ to form a shaped three dimensional body, we found that most of the sterilisation techniques that would be typically employed to sterilise a material are unsuitable or are incapable of sterilising the composition without degradation. The same was true in attempting to find a route to sterilise a two part adhesive or sealant.

Established terminal sterilisation procedures give a $10^6$ confidence in its sterility. We investigated heat as a route to sterilise these reactive materials.

Medical instruments such as scalpels etc. are typically steam sterilised using autoclaves. Typical steam sterilization cycles include a hold at 121° C. for a minimum of 15 minutes or a hold at 134° C. for a minimum of 3 minutes. Sterilisation of packaged items, in the absence of water, follow dry heat sterilisation processes which require higher temperatures and/or longer hold times. Various temperatures and hold times are known dependent on the materials and sterilization equipment employed. The US Pharmacopeia indicates 160-170° C. with a hold of 2-4 hours, the British Pharmacopeia indicates not less than 160° C. with a hold of not less than 1 hour and the Pharmacopeia Nordica states 180° C. with a hold of 30 minutes.

However the Tg and softening point of most commercially available thermoplastics which would be considered for packaging is below 160° C. The lack of readily available packaging which can withstand the required heat cycle is an obstacle to the use of a heat sterilisation method for sterilising RTV-2 compositions. Whilst some softening and reforming of packaging might be considered to be acceptable if resulting in intact packaging after sterilisation, the softened packaging might be permeable to or damage the performance of composition constituents or might allow the possibility of contamination thereof. Any external influence might disadvantageously reduce the effectiveness of the resulting cured composition.

SUMMARY

We have now found a route for sterilisation of packaged RTV-2 compositions, for which both the composition itself and the selected packaging are capable of withstanding conditions of elevated temperature for periods sufficient for sterilisation, without degradation thereof.

Accordingly, there is provided according to a first embodiment of the present invention a curable composition, comprising or apportioned between at least one Part A and at least one Part B, the Parts sealed within barrier means in manner to prevent contamination thereof, the composition comprising:
(i) one or more alkenyl-containing prepolymers having at least one alkenyl moiety per molecule,
(ii) one or more SiH-containing prepolymers having at least one SiH unit per molecule, and additionally:
(iii) a catalyst for curing by addition of alkenyl-containing prepolymer (i) to SiH-containing prepolymer (ii),
wherein the at least one Part A and at least one Part B are provided within or upon at least two respective receptacles or supports and are adapted to be dispensed or released therefrom in cooperative manner facilitating intimate contact and curing thereof, wherein the receptacle(s) or support(s) for at least one of Part A and Part B is thermally stable at elevated temperature of or in excess of 123° C. for a period in excess of 18 hours.

In a first preferred embodiment of the present invention there is provided a curable composition, comprising or apportioned between at least one Part A and at least one Part B, the Parts sealed within barrier means in manner to prevent contamination thereof, the composition comprising:
(i) one or more alkenyl-containing prepolymers having at least one alkenyl moiety per molecule,
(ii) one or more SiH-containing prepolymers having at least one SiH unit per molecule, and additionally:
(iii) a catalyst for curing by addition of alkenyl-containing prepolymer (i) to SiH-containing prepolymer (ii),
wherein the at least one Part A and at least one Part B are provided within at least two respective receptacles and are adapted to be dispensed therefrom in cooperative manner facilitating intimate contact and curing thereof, wherein the receptacle(s) for at least one of Part A and Part B is thermally stable at elevated temperature of or in excess of 123° C. for a period in excess of 18 hours.

In a further preferred embodiment of the invention there is provided a foamable curable composition for use as a negative pressure wound therapy wound filling material, comprising or apportioned between at least one Part A and at least one Part B, the Parts sealed within barrier means in manner to prevent contamination thereof, the composition comprising:
(i) one or more alkenyl-containing prepolymers having at least one alkenyl moiety per molecule,
(ii) one or more SiH-containing prepolymers having at least one SiH unit per molecule, and additionally:
(iii) a catalyst for curing by addition of alkenyl-containing prepolymer (i) to SiH-containing prepolymer (ii),
(iv) a blowing agent,
wherein the at least one Part A and at least one Part B are provided within at least two respective receptacles and are adapted to be dispensed therefrom in cooperative manner facilitating intimate contact and curing thereof, and formation of a porous foam which is suitable for transmitting a negative pressure to a wound surface. Preferably the receptacle(s) for at least one of Part A and Part B is thermally stable at elevated temperature of or in excess of 123° C. for a period in excess of 18 hours. Preferably the at least one Part A and at least one Part B are adapted to be dispensed in cooperative manner facilitating intimate contact and curing thereof and formation of a porous foam which is capable of transmitting negative pressure.

In a further preferred embodiment of the invention there is provided a curable composition, comprising or apportioned between at least one Part A and at least one Part B, the Parts sealed within barrier means in manner to prevent contamination thereof, the composition comprising:
(i) one or more alkenyl-containing prepolymers having at least one alkenyl moiety per molecule,
(ii) one or more SiH-containing prepolymers having at least one SiH unit per molecule, and additionally:
(iii) a catalyst for curing by addition of alkenyl-containing prepolymer (i) to SiH-containing prepolymer (ii),
wherein the at least one Part A and at least one Part B are provided upon at least two respective supports and are adapted to be released therefrom in cooperative manner facilitating intimate contact and curing thereof, wherein the support(s) for at least one of Part A and Part B is thermally stable at elevated temperature of or in excess of 123° C. for a period in excess of 18 hours.

In the above embodiments, the composition is sterilisable or is sterile. Preferably the composition is provided in packaged form, the receptacles or supports and any other integral parts sealed within further barrier means. The composition may be packaged prior to sterilisation or may be maintained under sterile conditions and packaged subsequent to sterilisation. Suitably therefore the composition is packaged as a double wrapped item, which allows for the removal of the first layer of sterile sealed packaging to reveal a cartridge or syringe which is completely sterile inside and out, facilitating entry into a sterile environment. If the product is only available in a single sterile packaging it would mean the external surface of the dispenser was contaminated and therefore it would not be possible to take into a sterile field Preferably the receptacle or support(s) for at least one of part A and part B as hereinbefore defined is thermally stable under conditions suitable for dry-heat sterilisation of the composition part. Preferably the prepolymers (i) and (ii) and catalyst (iii) are apportioned in at least two parts A and B in manner to provide respective parts A and B which in isolation are not reactive at ambient temperature. Preferably the Part A and Part B are provided sealed within receptacles or on supports in substantial absence of air within the receptacles or on the supports. Preferably receptacles or supports and any other components in or on which the Parts are supported are moisture and air and contaminant impermeable. Preferably the Part A and Part B are provided sealed within receptacles or on supports consisting exclusively of primary contact packaging materials that are capable of containing the composition at elevated temperature as herenbefore defined without thermal degradation thereof, and moreover which are capable of containing the composition at elevated temperature as herenbefore defined in manner so as not to contaminate the composition, i.e. do not interact with or degrade the respective Parts sealed therein or thereon.

We have found that the at least one Part A and/or at least one Part B as hereinbefore defined, are both stable and do not pre-react and also do not suffer contamination by or leakage of material from their respective receptacle or support at elevated temperature in excess of 110° C., and potentially up to 250° C. In the case that at least one of Part A and Part B is capable of sterilisation by an alternative technique, then only the other(s) of Part A and Part B need be packaged and sterilised. Alternatively the receptacles or supports for both of the at least one Part A and at least one Part B are thermally stable at elevated temperature of 123° C. for a period in excess of 18 hours. This allows both or all parts of the composition to be sterilised by thermal technique.

We have surprisingly found that while a standard 121° C. autoclave cycle for 15 minutes will not sterilise the composition, temperatures which are not as aggressive as the Pharmacopeiea standard 160° C. for 1 hour, for dry heat sterilisation, but when used for a sufficient period of time, in the region of 123° C. for 24 hours or more or 134° C. for 6 hours or more, nevertheless achieve the required level of sterilisation by the dry heat method. These temperatures are therefore emminently suited for providing a terminally sterile RTV-2 composition, hitherto unknown and unavailable.

Embodiments of the invention have application to any RTV, LTV or HTV compositions, which may comprise 2 or more components or Parts. Preferably the composition is an RTV-2, LTV-2 or HTV-2 composition, foamable or otherwise, for any envisaged use requiring sterility. The addition cure chemistry of 2-part RTV, LTV and HTV compositions is based on the hydrosilylation of vinyl functional prepolymers by Si-hydride functional prepolymers. Room temperature vulcanising is typically taken to mean the system cures below 50° C. Low temperature vulcanising is taken to mean the system cures in the range from 50° C. to 130° C. High temperature vulcanising is taken to mean the system cures at a temperature in excess of 130° C. More preferably the composition is an RTV-2 composition.

Embodiments of the invention may also have application to any two or more Part curable composition for which the Parts are adapted to be dispensed or released in cooperative manner facilitating intimate contact and curing thereof. Such Parts are therefore suitably fluid phase or capable of fluid behaviour under acceptable dispensing or release conditions or capable of wetting out a surface or material to which they are dispensed or released, for example Part A and Part B are capable of mutual wetting out when cooperatively dispensed or cooperatively released.

Suitably therefore the composition is packaged in a range of materials which would not withstand the standard 160° C./1 hour cycle, and yet will withstand terminal heat sterilisation conditions, and therefore removes the constraint limiting the design of the packaging and increases the commercial viability of the packaging. Furthermore heat sterilisation at this temperature is in the capability of most autoclaves or ovens. In a preferred embodiment a receptacle or support is thermally stable at elevated temperature in the range 123° C. to 145° C. for a period in excess of 18 hours down to 4 hours.

Polymers can often withstand elevated temperatures around or in excess of their thermal stability threshold, for short periods, but not for continuous prolonged periods. The dry heat sterilisation temperature can therefore be correlated against both the time at sterilisation temperature required to achieve 100% microbial kill, (hereinafter reference to 100% microbial kill is to the technically termed $10^6$ microbial kill (99.9999%)) and against the time at elevated temperature which the composition packaging is capable of withstanding without becoming thermally unstable. That the kill time and thermal stability time are related in similar manner to the sterilising temperature is fortuitous, and this underlies certain preferred embodiments.

Reference to dry heat sterilisation is to the sterilisation regime taking place directly at the composition Part. Accordingly the composition may be sterilised in a conventional oven or autoclave at ambient or elevated pressure with steam present, but the manner of packaging is resilient to steam penetration and thereby prevents steam contacting the composition directly, whereby the effective sterilisation is a dry heat sterilisation. The conditions prevailing outside the composition packaging are therefore irrelevant to those prevailing within the packaging, as steam does not penetrate the packaging, Accordingly a composition which is subject to dry heat sterilisation conditions but which includes water or moisture, would undergo a steam sterilisation regime. Conversely a composition which is subject to steam sterilisation conditions but which has no water or moisture present, would undergo an in situ dry heat sterilisation regime. Accordingly references to dry heat sterilisation as being unsuccessful are misleading, in the case that the in situ sterilisation regime conducted was in fact steam sterilisation.

Preferably either or both Parts of the composition have substantially no water, steam or air present and undergo an in situ dry heat sterilisation. More preferably Part B has substantially no water, steam or air present and undergo an in situ dry heat sterilisation. Part A may have water, moisture or air present or absent and may undergo steam or dry heat sterilisation.

Preferably the receptacles or supports are thermally stable at elevated temperature in the range 110 C to 250 C for a period in excess of 15 minutes, more preferably in the range of 110 C to 160 C for a period in excess of 30 minutes, more preferably in the range of 110 C to 155 C for a period in excess of 1 hour, more preferably in the range of 110 C to 145 C for a period in excess of 3 hours, more preferably in the range of 110 C to 135 C for a period in excess of 5 hours, more preferably in the range of 110 C to 120 C for a period in excess of 10 hours. This is represented graphically as the area above the line in FIG. 16.

Preferably the receptacles or supports are thermally stable at elevated temperature of 123° C. for a period of 18 hours or more. More preferably the receptacles or supports are thermally stable at any one or more of the following cycles selected from elevated temperature of 121° C. for a period of 30 hours, elevated temperature of 123° C. for a period of 24 hours, elevated temperature of 134° C. for a period of 6 hours and elevated temperature of 160° C. for a period of 1 hour. Cycles intermediate these values can be envisaged such as elevated temperature of 155° C. for a period of 2 hours, elevated temperature of 145° C. for a period of 4 hours.

The hereinbefore defined thermal cycles may be useful to determine intermediate elevated temperature and time combinations which would fall on or about an exponential curve drawn between the ends of the defined range as indicated in FIG. 17 (not to scale). Receptacles or supports which are thermally stable in the range between a first elevated temperature from a first period up to a second elevated temperature for up to a second period, are required to be stable at a single temperature and time combination in that range although they may also be stable across the entire range.

Reference herein to a thermally stable receptacle or support is to such article which exhibits no detectable change in one or more of the following property at the hereinbefore or hereinbelow defined temperature for the hereinbefore or hereinbelow defined period: melt flow index (MFI); or for which one of the following temperatures is not exceeded by the hereinbefore defined temperature and time: vicat (A) softening temperature, product specification maximum working temperature, thermal instability threshold temperature and the like.

Thermoplastics do not have a definite melting point which precisely marks the transition from fluid to solid, but rather undergo a gradual softening as temperature increases, or as time held at elevated temperature increases. For example polycarbonate has a Tg of about 150° C. and Vicat softening temperature (10N load) of 157° C., and softens gradually around this temperature. Melt Flow Index is a measure of the ease of flow of the melt of a thermoplastic polymer (ASTM D1238, ISO 1133). Vicat softening point is the determination of softening point for such materials that have no definite melting point. It is taken as the temperature at which the specimen is penetrated to a depth of 1 mm by a flat-ended needle with a 1 square mm circular or square cross-section loaded with a 10N load (Vicat A). See Polymer Handbook, ed. J. Brandrup and E. H. Immergut, John Wiley & Sons Inc., New York, $2^{nd}$ edn., 1975, pp. 111-144, the contents of which are incorporated herein by reference.

Receptacles or supports may therefore comprise any suitable material which provides a barrier to microbial infection and is thermally stable at temperatures in excess of 123° C. up to 160° C. and even up to 250° C. Certain materials such as some polyethylene (PE) for example polyethylene terephthalate (PET), PE (Vicat softening temperature 94-107° C., ultra high MW PE (UHMPE) (Vicat softening temperature 80-100° C.), certain grades of polypropylene (PP) are of low thermal stability and are therefore not suitable for the invention. Certain preferred embodiments use of known and novel high temperature stable materials such as polycarbonates (PC) (Vicat softening temperature 157° C.), isotactic polypropylene (iPP) (Tg −13° C. to 0° C., Vicat softening temperature 138-155° C.), atactic polypropylene (aPP) (Tg −18° C. to −5° C.), polymethylpentene (PMP) and cyclic olefin copolymers (COC) (Tg and Vicat 80° C.-180° C.) which are disclosed as stable up to 170° C. Because COC is amorphous, it maintains stiffness at elevated temperature far better than semicrystalline polymers such as PE or PP. COC maintains high stiffness up to temperatures within 10° to 15° C. of its Tg. Because iPP has Tg remote from its Vicat softening temperature it has superior maintenance of mechanical properties at elevated temperature to COC and like materials having proximal Tg and Vicat softening temperature.

Preferably thermally stable receptacles, supports and any seals and cooperating parts are comprised of materials selected from metals, glass, and polymers and the like and from composites, laminates and combinations thereof which are thermally stable at elevated temperature of 123 C for a period of or in excess of 18 hours; preferably from PE, PP PMP, COC's, metal foil, glass, solid phase silicone polymer and the like and from composites, laminates and combinations thereof which are thermally stable at elevated temperature of 123 C for a period in excess of 18 hours;
more preferably from:
high temperature stable PE such as high density PE (HDPE) which can withstand temperatures of 120° C. for short periods, or 110° C. continuously, and cross linked PE (PEX or XLPE) with reduced flow tendency at up to 120°-150° C.;
high temperature stable PP (HTSPP) such as isotactic PP (iPP Vicat softening temperature 138-155° C., W. A. Lee and R. A Rutherford "The glass transition temperatures of polymers" in Polymer Handbook, ed. J. Brandrup and E. H. Immergut, John Wiley & Sons Inc., New York, $2^{nd}$ edn., 1975, pp. V-27, the contents of which are incorporated herein by reference.); atactic PP;
commercially available PP rated to 140° C., Tg approx −10° C.;
PCs (Vicat softening temperature 157 C);
polymethylpentene (PMP, for example available as 50 ml squat form beaker, temperature resistant to 180° C., Fisher Scientific, Product Code: BNH-740-070E);
high temperature stable COC's (Tg and Vicat 110° C.-180° C.);
metal foil for example aluminium;
glass;
solid phase silicone polymer;
and the like;
and from composites, laminates and combinations thereof which are thermally stable as hereinbefore defined. PCs, HTSPP, COCs and glass are preferred materials.
More preferably compositions comprise receptacle or support material having thermal stability at temperatures in the range as follows:
155° C. to 160° C.: COCs, PCs, metal foil, glass, silicone polymer;
110° C. to 155° C.: COCs, PCs, PEX or XLPE, isotactic PP, HDPE.

Suitably the barrier means, for example a receptacle seal, closure, cap, lid or the like is thermally stable as hereinbefore defined. Certain compositions may be suitable for use together with cooperating parts facilitating containment, dispensing or release of the at least one Part A and at least one Part B and intimate contact thereof. Such cooperating parts may optionally be thermally stable and dry heat sterilisable as hereinbefore defined or steam sterilisable, or may be provided for assembly with cooperating parts during use, and parts may be sterilised by alternative means and are not required to be thermally stable as hereinbefore defined. In the case that the packaged composition comprises integral cooperating parts, any such parts are suitably thermally stable as hereinbefore defined. Integral cooperating parts include closures such as lids, caps, seals such as O-rings, release means such as pistons, plungers and the like.

Suitably the composition including receptacles or supports and any integral cooperating means is packaged in a further outer (secondary) packaging which is resistant to EO or is steam permeable, which is suitable for sterilisation in usual manner. Thereby both the interior and exterior of the composition are maintained sterile, and can be carried into a sterile field and opened.

We have determined that some compositions may be susceptible to contamination at thermal sterilisation conditions, by contact with receptacle and cooperating parts. Accordingly cooperating parts which are themselves thermally stable have been found to contaminate the Part A and/or Part B components at elevated temperature. Contamination takes the form of one or more of visual contamination, chemical contamination and the like. Visual contamination is for example discoloration or formation of agglomerates. Chemical contamination is for example one or more of viscosity change, reducing activity of or deactivating components which take part in curing or foaming reaction.

A preferred composition comprises Part A and Part B as hereinbefore defined provided within or upon receptacles or supports wherein cooperating parts for such receptacles or supports are thermally stable at elevated temperature of 123° C. for a period in excess of 18 hours, and optionally at preferred elevated temperature conditions as hereinbefore defined.

Preferably a composition can comprise Part A and Part B as hereinbefore defined provided within or upon receptacles or supports wherein Part A and Part B are thermally stable at elevated temperature of 123° C. for a period of or in excess of 18 hours, and optionally at preferred elevated temperature conditions as hereinbefore defined, in the presence of or in contact with cooperating parts for such receptacles or supports. Preferably such cooperating parts are substantially inert in the presence of Part A and/or Part B under such conditions, i.e are both thermally stable and also remain intact under the thermal sterilisation conditions, i.e do not leach out any component.

A receptacle or support may be flexible or rigid. A rigid receptacle or support is suitably any vial or cartridge as known in the art. A flexible receptacle or support for example may be formed from a laminate of metal foil having on each face thereof a film of thermally stable polymer as hereinbefore defined, which can be heat-sealed or laminated.

A receptacle may comprise a portion which is intended to remain intact, and a portion which is intended for rupture or penetration in manner to release the composition Part sealed therein. A receptacle may therefore comprise a combination of different thermally stable materials or a combination of different thicknesses of a thermally stable material.

Receptacles may be manually ruptured at weakened portions thereof, or mechanically ruptured or penetrated by physical means for example provided in a device for penetration and cooperative dispensing of composition parts. Suitable physical means include needles, spikes, punches such as bayonet caps, push-fit opening means and the like.

Reference herein to Parts A and B being present in receptacles in substantial absence of air or moisture, is suitably to air or moisture presenting less than 10% of the receptacle volume, preferably less than 5% of the receptacle volume. Air or moisture is suitably absent from any space above or about the composition, i.e headspace or the like, or such space is substantially absent. Air or moisture may additionally be absent from the composition itself, i.e the composition may be degassed or sparged or the like to remove air. It will be appreciated that the objective of providing an absence of air is to provide an absence of oxygen and moisture vapour.

Accordingly a substantial absence of air may be provided in known manner by displacement and/or removal or air. Displacement of air is suitably by means of purging the space about the composition, such as the headspace present above the composition within the barrier means, with a suitable inert gas; and/or sparging the composition with a suitable inert gas. Removal of air is suitably by means of providing the Part in a receptacle of substantially equal volume to the Part volume in manner to substantially eliminate any headspace. A suitable inert gas is argon or nitrogen or the like. Purging displaces air above the Part with inert gas. Sparging displaces air within the Part with inert gas. Matching volumes removes air above the Part.

Reference to cooperative dispensing as hereinbefore defined is to any method by which one or more Parts is dispensed simultaneously with and into direct contact with the other one or more Parts, preferably with simultaneous mixing. Preferably receptacles are adapted to be received within a device providing means to cooperatively release the respective Parts into an integral mixing chamber or nozzle with integral advancing mixing means for ejecting mixed composition from the device. Suitably ejection means is provided for dispensing of composition from receptacles, for example pistons, plungers and the like. Embodiments herein may be of particular advantage in ejecting composition directly into or onto the site of application or into a mould prior to application, thereby minimising the risk of contamination or infection. This has further advantages of enhancing accuracy of administering composition.

In a particular advantage of the invention certain compositions may be suitable for cooperatively dispensing into a desired location or cavity, curing and retaining a desired positioning or shape. Preferably the composition is suitable for dispensing into or about a wound. Preferably the composition is suitable for dispensing or releasing in a sterile field or environment. This is particularly advantageous in the case of medical applications for example within the sterile field of an operating theatre allowing the possibility to dispense directly or indirectly, for example via a mould, into a wound in a sterile field or environment. This avoids the need to contact the composition once dispensed, for example for positioning or shaping, and minimises the risk of introducing infection.

An embodiment of the RTV-2 composition may comprise any prepolymers that follow a hydrosilylation reaction. One prepolymer preferably contains alkenyl groups, the other preferably contains Si—H moieties. The group of siloxane polymers is based on a structure comprising alternate silicon and oxygen atoms with various organic moieties attached to the silicon. Curing can be defined as a treatment that decreases the flow of an elastomer. This change is generally brought about by linking reactions between polymer molecules. Where the silicon hydride (Si—H) moiety is part of a polysiloxane, it is possible for the alkenyl group to either be part of a siloxane prepolymer or otherwise part of a non-siloxane prepolymer. The position of the alkenyl functional group is not critical and it may be either at the molecular chain terminals or in non-terminal positions along the molecular chain.

Prepolymers (i) and (ii) are commercially available or may be obtained by known techniques. Suitably prepolymers (i) and/or (ii) are independently selected from known and novel fluid phase homopolymeric, and copolymeric prepolymers, and their entangled systems and mixtures thereof. The compositions, in turn, cure to form copolymers, and may also include their entangled systems and mixtures with other non-reactive prepolymers if present in the composition.

The term fluid phase is intended to include prepolymers which can exist in fluid phase or behave as fluids, i.e the sterilised prepolymers are capable of admixture to form the respective Part.

Copolymeric prepolymers include all hybrids derived from two or more monomeric species, including alternating, periodic, statistical, random, block, linear, branched, star, graft and pendant copolymers. Entangled systems include interpenetrating networks (IPNs) and semi-interpenetrating networks (SIPNs). It is also the case that these prepolymers can incorporate both organic and inorganic moieties.

Preferably prepolymers (i) and (ii) are selected from silicones, including siloxanes and modified siloxanes, polyurethanes (PU) including polyester and polyether urethanes, elastomeric polyether polyesters, polyglycolic acid, polyacetates such as ethyl vinyl acetate, polyacrylate, polyacid derivatives of polysaccharides, such as carboxyalkylcellulose, carboxyalkylchitosan and copolymers thereof, and their hybrids including copolymers, entangled systems and mixtures thereof.

More preferably the curable composition makes use of an addition cure reaction between organohydrogensiloxane units and organoalkenylsiloxane units. These units may be incorporated into a wide range of polymeric, copolymeric, entangled and mixed prepolymers as hereinbefore defined. Preferred siloxane prepolymers (i) and (ii) therefore include these respective units and are more preferably polyorganosiloxanes.

Examples of hybrid organic-inorganic polymeric systems that have used both siloxane and organic units include: acrylate functionalized siloxane copolymers, which have found use in contact lenses (U.S. Pat. No. 3,808,178); hybrid grafts where organic polymers are grafted onto a polysiloxane chain or where siloxanes are grafted onto organic polymers, for example in silane graft technology for cross linkable HDPE (U.S. Pat. No. 3,646,155) where hybrid grafts have been used to allow the cross linking of organic polymers through siloxane bond formation; hybrid block copolymers for example silicone-polycarbonate block copolymers (U.S. Pat. No. 3,274,155); and copolymers of hybrids of silicone and ethylene copolymers, cross-linked with vinyl-containing silicone copolymers which have found use in coating textiles (US 2005/0100692);

IPNs represent a special class of hybrid polymeric systems, these systems use a combination of mechanical entanglement and crosslinking in which one polymer is cured about another; these include thermoplastics entangled with platinum catalyzed addition cure silicones such as silicone-urethane IPNs and semi-IPNs including silicone-urethane and silicone-polyamide systems which are of general application or have found specific use in coating textiles (U.S. Pat. Nos. 4,714,739, 7,543,843); hydrophilic components immobilised in a silicone polymer (U.S. Pat. No. 5,397,848) which have found use as contact lens material; and silicone polymer cured about a non-reactive polymer of comparable adhesion, which have found use in coating textiles (U.S. Pat. No. 7,132,170).

Prepolymers may also be selected from modified silicones (MS) which find use as adhesives in catheter tubing and the like.

Preferred compositions comprise a polydiorganosiloxane prepolymer (i) and/or (ii) and/or their respective combinations with the aforementioned prepolymers. A composition in which prepolymers comprise or consist essentially of polydiorganosiloxane prepolymers (i) and (ii) has particular advantages, for example in applications where low toxicity is an advantage, preferably in medical or dental applications or in non-medical or non-dental applications requiring low toxicity or favorable biocompatibility.

Prepolymer (i) and (ii) may comprise respective alkenyl-containing units and organohydrogensiloxane units situated along the length of prepolymer chains, and/or as prepolymer chain end-capping units or a combination thereof. Prepolymer (i) in-chain and end-capping alkenyl units preferably comprise alkenyl group or moiety $R^{Alk}$ selected from $C_{2-20}$ alkenyl optionally substituted or including one or more aryl groups or moieties. $R^{Alk}$ may comprise terminal or non terminal unsaturation, and may be of the formula i-I:

in which the groups $R^{Alk1}$ and $R^{Alk2}$ are independently selected from H, $C_{1-20}$ alkyl and $C_{5-20}$ aryl groups and combinations thereof and a moiety $R^{Alk1}$ is selected from a single bond, $C_{1-20}$ alkyl and $C_{5-20}$ aryl groups and combinations thereof. One of $R^{Alk2}$ may be a moiety linking to polymer chain. More preferably each $R^{Alk}$ is independently selected from vinyl, allyl, propenyl, and from terminally and non-terminally unsaturated butenyl, pentenyl, hexenyl, heptenyl, octenyl, nonenyl and decenyl groups, most preferably selected from vinyl and hexenyl groups and moieties.

Preferably prepolymer (i) comprises a polydiorganosiloxane polymer or copolymer comprising alkenyl-containing units of the formula (i-II):

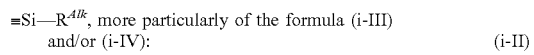

wherein $R^{Alk}$ is as hereinbefore defined and one or more groups $R^1$ are organo groups suitably independently selected from alkyl and aryl groups, more preferably optionally fluorinated $C_{1-20}$ alkyl and cycloalkyl and $C_{5-20}$ aryl groups and combinations thereof, for example from methyl, ethyl, propyl, butyl, pentyl, hexyl, heptyl, octyl, nonyl and/or decyl groups.

More particularly prepolymer (i) is selected from the formula i-V and i-VI:

$P^i$—O—Si $R^1{}_2R^{Alk}$ wherein $P^i$ denotes the remainder
of the polymer chain which may incorporate
same or different units, and $R^1$ is as hereinbe-
fore defined.                                                                    i-VI Prepolymer (i) may also comprise a polyorganosiloxane exhibiting, per molecule, at least two $C_2$-$C_6$ alkenyl groups bonded to the silicon and having, for example, a viscosity of between 10 and 300 000 mPa·s, which can in particular be formed of at least two siloxyl units of formula:

$$Y_d R_e SiO_{\frac{(4-d-e)}{2}} \quad \text{(III)}$$

in which:
Y is a $C_{2-6}$ alkenyl such as vinyl, allyl or hexenyl groups, preferably vinyl,
R is a monovalent hydrocarbon group with no unfavorable effect on the activity of the catalyst which is generally chosen from alkyl groups having from 1 to 8 carbon atoms inclusive, such as the methyl, ethyl, propyl and 3,3,3-trifluoropropyl groups, cycloalkyl groups, such as the cyclohexyl, cycloheptyl and cyclooctyl groups, and aryl groups, such as xylyl, tolyl and phenyl,
d is 1 or 2, e is 0, 1 or 2 and d+e=1, 2 or 3,
optionally all the other units being units of average formula:

$$R_f SiO_{\frac{4-f}{2}} \quad \text{(IV)}$$

in which R has the same meaning as above and f=0, 1, 2 or 3.

Examples of prepolymer (i) are, for example, dimethylpolysiloxanes comprising dimethylvinylsilyl ends, (methylvinyl)(dimethyl)polysiloxane copolymers comprising trimethylsilyl ends or (methylvinyl)(dimethyl)polysiloxane copolymers comprising dimethylvinylsilyl ends.

A convention accepted in the art for denoting the units of silicones according to the number of oxygen atoms bonded to the silicon is used here. This convention uses the letters M, D, T and Q (abbreviations for "mono", "di", "tri" and "quatro") to denote this number of oxygen atoms. This nomenclature of silicones is described, for example, in the work by Walter Noll, "Chemistry and Technology of Silicones", Academic Press, 1968, 2nd edition, on pages 1 to 9.

Prepolymer (i) may also be a silicone resin bearing at least two alkenyl, preferably vinyl groups. Such silicone resin comprising at least two different siloxane units chosen from those of M siloxane unit of formula $R_3SiO_{1/2}$, D siloxane unit of formula $R_2SiO_{2/2}$, T siloxane unit of formula $RSiO_{3/2}$ and Q siloxane unit of formula $Si_{4/2}$,
wherein R denotes a monovalent hydrocarbon group, with the conditions that at least one of these siloxane units being a T or Q siloxane unit and that at least two of the M, D and T siloxane units comprises an alkenyl group.

The silicone resin could be selected from the group consisting of:
an organopolysiloxane resin of formula $MT^{Vi}Q$ consisting essentially of:
  (a) trivalent siloxane units $T^{Vi}$ of the formula $R'SiO_{3/2}$;
  (b) monovalent siloxane units M of the formula $R_3SiO_{1/2}$, and
  (c) tetravalent siloxane units Q of the formula $SiO_{4/2}$
an organopolysiloxane resin of formula $MD^{Vi}Q$ consisting essentially of:
  (a) divalent siloxane units $D^{Vi}$ of the formula $RR'SiO_{2/2}$;
  (b) monovalent siloxane units M of the formula $R_3SiO_{1/2}$, and
  (c) tetravalent siloxane units Q of the formula $SiO_{4/2}$
an organopolysiloxane resin of formula $MDD^{Vi}Q$ consisting essentially of:
  (a) divalent siloxane units $D^{Vi}$ of the formula $RR'SiO_{2/2}$;
  (b) divalent siloxane units D of the formula $R_2SiO_{2/2}$
  (b) monovalent siloxane units M of the formula $R_3SiO_{1/2}$, and
  (c) tetravalent siloxane units Q of the formula $SiO_{4/2}$
an organopolysiloxane resin of formula $M^{Vi}Q$ consisting essentially of:
  (a) monovalent siloxane units $M^{Vi}$ of the formula $R'R_2SiO_{1/2}$; and
  (b) tetravalent siloxane units Q of the formula $SiO_{4/2}$, and
an organopolysiloxane resin of formula $M^{Vi}T^{Vi}Q$ consisting essentially of:
  (a) monovalent siloxane units $M^{Vi}$ of the formula $R'R_2SiO_{1/2}$;
  (b) trivalent siloxane units $T^{Vi}$ of the formula $R'SiO_{3/2}$, and
  (c) tetravalent siloxane units Q of the formula $SiO_{4/2}$
wherein R denotes a monovalent hydrocarbon group such as methyl and R' denotes a vinyl group:

Such resins are well-known branched organopolysiloxane oligomers or polymers which are commercially available. They are provided in the form of solutions, preferably siloxane solutions.

Prepolymer (ii) in-chain and end-capping polyorganohydrogensiloxane units are preferably selected from the formula ii-I and ii-II:

| | |
|---|---|
| —O—Si $R^2$H—O— | ii-I |
| —O—Si $R^2_2$H, more preferably prepolymer (ii) is selected from formula ii-III and ii-IV: | ii-II |
| $P^{ii}$—O—Si $R^2_2$H—O—$P^{ii}$ | ii-III |
| $P^{ii}$—O—Si $R^2_2$H wherein | ii-IV |

$P^{ii}$ denotes the remainder of the polymer chain which may incorporate same or different units and one or more groups $R^2$ are organo groups suitably independently selected from optionally fluorinated $C_{1-20}$ alkyl and cycloalkyl, $C_{5-20}$ aryl and combinations thereof, for example from methyl, ethyl, propyl, butyl, pentyl, hexyl, heptyl, octyl, nonyl and/or decyl groups.

Prepolymer (ii) preferably comprises a polyorganohydrogensiloxane-polydiorganosiloxane copolymer, incorporating one or more units ii-I and/or ii-II:

| | |
|---|---|
| —O—Si $R^2$H—O— | ii-I |
| —O—Si $R^2_2$H and one or more units ii-V and/or ii-VI: | ii-II |
| —O—Si $R^2_2$—O— | ii-V |
| —O—Si $R^2_3$ wherein $R^2$ is as hereinbefore defined, more preferably copolymer incorporating polyorganohydrogensiloxane end-capping units, i.e prepolymer chains terminate with the group or moiety ii-VII: | ii-VI |
| ≡Si—H, more particularly with the unit of formula ii-II: | ii-VII |

—O—Si R²₂H as hereinbefore defined. Most preferably prepolymer (ii) comprises methylhydrogensiloxane-dimethylsiloxane copolymers.     ii-II Prepolymer (ii) may also comprises a polyorganosiloxane, exhibiting, per molecule, at least two hydrogen atoms bonded to the silicon and preferably at least three ≡SiH units and having, for example, a viscosity of between 1 and 5000 mPa·s, which can in particular be formed of siloxyl units of formula:

$$H_g X_i SiO_{\frac{4-g-i}{2}} \quad (V)$$

in which:
X is a monovalent hydrocarbon group with no unfavorable effect on the activity of the catalyst which is generally chosen from alkyl groups having from 1 to 8 carbon atoms inclusive, such as the methyl, ethyl, propyl and 3,3,3-trifluoropropyl groups, cycloalkyl groups, such as the cyclohexyl, cycloheptyl and cyclooctyl groups, and aryl groups, such as xylyl, tolyl and phenyl,
g=1 or 2, preferably=1, i=0, 1 or 2 and g+i=1, 2 or 3, optionally all the other units being units of average formula:

$$X_j SiO_{\frac{4-j}{2}} \quad (VI)$$

in which X has the same meaning as above and j=0, 1, 2 or 3.

Examples of prepolymer (ii) are polymethylhydrosiloxanes or methylhydrodimethylsiloxane copolymers.

Alternatively or additionally prepolymers (i) and (ii) are as defined in U.S. Pat. No. 5,153,231 for Cavi-Care RTV-2 type compositions, also as defined in US 2006/0217016, U.S. Pat. Nos. 3,928,629 and 4,529,553, 4,714,739 and US2002/0010299 the contents of which are incorporated herein by reference, or as commercially available (Rhodorsil RTFoam 3240, Mepiseal, Silpuran 2111 A/B, Silpuran 2400/18 A/B, and the like In the case that prepolymers include other units additional to iIII, iIV, iiII and iiIII for example, these are suitably not reactive with the respective prepolymer at ambient temperature or under sterilising conditions.

Suitably the ratio of silicon-bonded hydrogen atoms provided by (ii) to silicon-bonded alkenyl moieties provided by (i) is at least 0.5:1, preferably 1:1, Preferably, embodiments of the curable composition follows the catalysed addition cure reaction according to the following scheme:

P^i—R^{Alk1}—CR^{Alk1}=CR^{Alk2}₂P^{ii}—SiHR²R^{2/P} →^{[catalyst]}

P^i—R^{Alk1}—CHR^{Alk1}CR^{Alk2}₂—SiR²R^{2/P}P^{ii} more preferably:

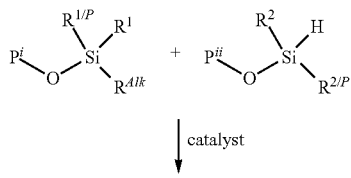

| catalyst

-continued

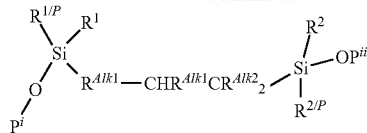

wherein integers are as hereinbefore defined and $R^{1/P}$ is selected from $P^i$ and $R^1$ as hereinbefore defined and $R^{2/P}$ is selected from $P^{ii}$ and $R^2$ as hereinbefore defined.

Suitably the prepolymers (i) and (ii) and catalyst (iii) are apportioned in at least one Part A and at least one Part B in manner to provide respective Parts A and B which in isolation are not reactive at ambient temperature, nor under sterilisation conditions. Apportioning may also be determined according to volume and viscosity. The at least one Part A and at least one Part B may be of substantially equal volume and viscosity or of different volume and/or viscosity. Part A or Part B may incorporate a suitable viscosity moderator or diluent, in amount to increase or reduce volume and/or viscosity. By this means Part A and Part B having different volume and viscosity may be volume and viscosity matched for improved ease and intimacy of mixing and dispensing. A suitable diluent is for example a silicone oil which is available in any desired viscosity for thickening or thinning effect. Advantageously we have found that Part A comprising a silicone oil is radiation sterilisable without deleterious effect on properties of the resultant cured composition.

In the case that Part A is of greater volume and higher viscosity than Part B, Part A may be apportioned between two or more Parts A1, A2 etc, of equal volume, providing 3 or more Parts A and B of approximately equal volume. Alternatively or additionally Part B may incorporate silicone oil as a substantially inert diluent and/or thickener.

In a preferred embodiment of the invention Part A incorporates an amount of (i) one or more polydiorganosiloxane prepolymers having at least one organoalkylenylsiloxane unit per molecule, and additionally (iii) a catalyst for curing by addition of prepolymer (i) organoalkylenylsiloxane to prepolymer (ii) organosiloxane, and Part B incorporates an amount of (i) one or more polydiorganosiloxane prepolymers having at least one organoalkylenylsiloxane unit per molecule, together with (ii) the one or more polydiorganosiloxane prepolymers having at least one organohydrogensiloxane unit per molecule. In this case, the volume and viscosity of Parts A and B may be approximately equal, in known manner.

In one composition, Part A incorporating the catalyst (iii) incorporates substantially only one of prepolymers (i) and (ii), preferably only prepolymer (i). If present prepolymer (ii) is present in trace amount insufficient to significantly react and significantly increase prepolymer viscosity at elevated temperature prior to mixing and curing. A significant viscosity increase is greater than 0% up to 5% by weight.

The Parts A and B are suitably comprised in respective receptacles in a volume of from 80 to 99.9% of the receptacle volume, preferably from 90 to 99.9% thereof, more preferably from 95 to 99.9% thereof, most preferably from 98 to 99.9% thereof. Receptacles may comprise respective one or more composition part or parts under an inert atmosphere or vacuum. The removal of air or water present in the receptacle is advantageous. This appears to minimise degradation as assessed by the appearance of the parts, after sterilisation.

A catalyst as hereinbefore defined may be any catalyst which is effective in catalysing the addition curing reaction as hereinbefore defined, more preferably as hereinabove illustrated. Suitable catalysts are selected from any known form of platinum, rhodium, palladium, nickel and like addition curing hydrosilylation catalysts, for example as disclosed in U.S. Pat. No. 5,153,231, US 2006/0217016, U.S. Pat. Nos. 3,928,629 and 4,529,553 the contents of which are incorporated herein by reference.

A platinum catalyst may be selected from platinum black, platinum as deposited on carriers including silica such as silica gel or carbon such as powdered charcoal, platinic chloride or chloroplatinic acid and alcohol solutions thereof, salts of platinic and chloroplatinic acids and platinum complexes such as platinum/olefin, platinum/alkenylsiloxane, platinum/beta-diketone, platinum/phosphine and the like. Chloroplatinic acid may be the hexahydrate or anhydrous form. A platinum complex may be prepared from chloroplatinic acid and its hexahydrate, or from platinous chloride, platinum dichloride, platinum tetrachloride and their neutralised complexes with divinyltetramethyldisiloxane, optionally diluted with dimethylvinylsiloxy endcapped polydimethylsiloxane.

A palladium catalyst may be selected from palladium on carbon, palladium chloride and the like.

A rhodium catalyst may be selected from rhodium chloride and one or more complexes of rhodium having the general formula iii-I or iii-II:

$$RhX_3(SR_2)_3 \quad \text{(iii-I)}$$

$$Rh_2(CO)_4X_2 \quad \text{(iii-II)}$$

wherein each X represents a halogen atom and each R represents an alkyl or aryl radical or combination thereof having from 1 to 8 inclusive carbon atoms or the $R'_3SiQ$ group in which Q represents a divalent aliphatic hydrocarbon radical having from 1 to 6 inclusive carbon atoms and R' represents an alkyl or aryl radical or combination thereof having from 1 to 8 inclusive carbon atoms or a $(CH_3)_3Si$— group, not more than one R' per molecule being $(CH_3)_3Si$—. For example rhodium chloride/di(n-butyl)sulfide complex and the like.

A nickel catalyst is preferably a zero valent nickel selected from) $M_2Ni^{(0)}$ such as bis(1,5-cyclo-octadienyl) nickel $(Ni(COD)_2)$ and from $MNi^{(0)}G$ wherein M is a bidentate alkene cyclic hydrocarbon ring of $C_{8-12}$ and G is selected from monodentate and bidentate phosphorous groups having hydrogen atoms, substituted or unsubstituted hydrocarbon radicals or mixtures thereof bonded to the phosphorous atoms of the phosphorous groups.

Preferably the composition comprises an addition-reaction retardant or a crosslinking inhibitor chosen, for example, from the following compounds:
  polyorganosiloxanes substituted with at least one alkenyl that may optionally be in cyclic form, tetramethylvinyltetrasiloxane being particularly preferred,
  organic phosphines and phosphites,
  unsaturated amides,
  alkyl maleates, and
  acetylenic alcohols.
These acetylenic alcohols (see FR-A-1 528 464 and FR-A-2 372 874), which are among the preferred thermal blockers of the hydrosilylation reaction, have the formula:

$$(R')(R'')C(OH)\text{—}C\equiv CH$$

in which formula
  R' is a linear or branched alkyl radical, or a phenyl radical;
  R" is H or a linear or branched alkyl radical, or a phenyl radical; the radicals R', R" and the carbon atom alpha to the triple bond possibly forming a ring; and
  the total number of carbon atoms contained in R' and R" being at least 5 and preferably from 9 to 20.
Examples that may be mentioned include:
  1-ethynyl-1-cyclohexanol;
  3-methyl-1-dodecyn-3-ol;
  3,7,11-trimethyl-1-dodecyn-3-ol;
  1,1-diphenyl-2-propyn-1-ol;
  3-ethyl-6-ethyl-1-nonyn-3-ol;
  2-methyl-3-butyn-2-ol;
  3-methyl-1-pentadecyn-3-ol.
These α-acetylenic alcohols are commercial products. Such a retardant is present in a maximum proportion of 3000 ppm relative to the total weight of the polyorganosiloxanes in the silicone composition. Methyl butynol could be chosen as in Cavi-Care.

The composition may be non-foamable or may be foamable, comprising (iv) a blowing agent, selected from any agent which evolves gas or vapour as part of or during the curing reaction, for example selected from H-donors, OH-containing agents, H-bonding agents such as:
  alcohols including methanol, ethanol, n-propanol, isopropanol, n-butanol, 2-butanol, tert-butanol, n-hexanol, n-octanol and benzyl alcohol. n-Propanol, n-butanol, n-hexanol and n-octanol are particularly preferred,
  polyols such as diols including, 4-butanediol, 1,5-pentanediol and 1,7 heptanediol,
  silane or polysilane having at least one silanol group, or water.

A foamable composition may produce a foam having any desired porosity or pore architecture. In a particular advantage a foamable composition provides an open-pore foam. A preferred foamable composition is adapted to deliver a foam of very high free internal volume, e.g. of the order of 70% to 90%. Preferred porous foams are of mechanical strength to prevent the foam structure collapsing in use, more preferably are adapted to form a cured three dimensional body which is resiliently deformable.

Preferably a foamable composition is adapted to deliver a foam which cures to form open interfaces with moist or wet surfaces. Such open-interface foams are suitable for communicating with wound surfaces via the foam body, for example. In a particular advantage we have found that such open-interface foams are provided by silicone compositions. In a further advantage the composition is suitable for providing a cured porous three dimensional body of desired shape.

The composition may be non-foamable or may be foamable, comprising (iv) a blowing agent, selected from any agent which evolves gas or vapour as part of or during the curing reaction, for example selected from H-donors, OH-containing agents, H-bonding agents such as:
  alcohols including methanol, ethanol, n-propanol, isopropanol, n-butanol, 2-butanol, tert-butanol, n-hexanol, n-octanol and benzyl alcohol. n-Propanol, n-butanol, n-hexanol and n-octanol are particularly preferred,
  polyols such as diols including, 4-butanediol, 1,5-pentanediol and 1,7 heptanediol,
  silane or polysilane having at least one silanol group, or water.

The composition may comprise active agents, which may have any desired activity for the intended purpose, for example medically active agents and the like. Suitable active agents or APIs are thermally stable as hereinbefore defined, preferably are stable under the required thermal cycle to achieve terminal sterility of the compositions disclosed herein. These are commonly selected from antimicrobial agents and disinfectants such as silver and derivatives including silver oxide, silver nitrate, silver acetate and silver chloride, biguanides including polyhexamethylene and chlorhexidine glucanate and its acetate salt, active agents such as pharmaceuticals, biocides, growth factors, hemostats and the like, nutrients, pain killers and agents to minimise discomfort and the like and combination materials.

Antimicrobial agents, biocides and disinfectants may be selected from silver, in particular nano crystalline silver, and derivatives including silver complexes and salts such as ionic silvers, silver zeolite, silver oxide, silver nitrate, silver acetate, silver chloride, silver sulphadiazine), biguanides including polyhexamethylene biguanide and chlorhexidine digluconate and its acetate salt chlorhexidine acetate and diacetate, manuka honey, peroxides (e.g. hydrogen peroxide), iodine (e.g. povidone iodine), sodium hypochlorite, copper, copper complexes; zinc (e.g. zinc oxide, zinc pyrithione), gold, gold complexes; phosphates, amines, amides and sulphonamides (e.g. hexatidine, proflavine, mafenide, nitrofurazone, norfloxacin; antibiotics (e.g. gentamicin, bacitracin, rifampicin; alcohols and acids (e.g. ethanol, phenoxy ethanol, mupirocin); known irradiation stable antimicrobials include Chlorhexidine acetate, silver sulphadiazine (SSD) and nano crystalline silver, these are active components of terminally sterile commercially available products Bactigras™, Allevyn Ag™ and Acticoat™ respectively; nutrients, pain killers and other pain management techniques suitably include analgesics and anasthetics and may be selected from amethocaine, lignocaine, non-steroidal anti-inflammatory drugs);

Heamostats may be selected from Chitin, chitosan, kaolin; Antifibrinolytics such as amino acids, aminocaproic acid, tranexamic acid, aminomethylbenzoic acid; Proteinase inhibitors including aprotinin, alfal antitrypsin, C1-inhibitor, camostat; Vitamin K and other hemostatics including vitamin K, phytomenadione, menadione; Fibrinogen including human fibrinogen; Local hemostatics including absorbable gelatin sponge, oxidized cellulose, tetragalacturonic acid hydroxymethylester, adrenalone, thrombin, collagen, calcium alginate, epinephrine; Blood coagulation factors including coagulation factor IX, II, VII and X in combination, coagulation factor VIII, factor VIII inhibitor bypassing activity, coagulation factor IX, coagulation factor VII, Von Willebrand factor and coagulation factor VIII in combination, coagulation factor XIII, eptacog alfa (activated), nonacog alfa, thrombin. Systemic hemostatics: etamsylate, carbazochrome, batroxobin, romiplostim, eltrombopag; combination materials including superabsorbers, Odour management, Wovens and non wovens, Gellable fibres; Growth factors, Wound debridements—mechanical, autolytic and enzymatic; Resorbable dressings and micro structure to influence cell ingrowth; Cells, tissue (e.g. autologous treatments); Indicators; Dyes and colourants.

Preferred compositions may include additional components selected from adjuvants, preservatives, extenders and the like. Adjuvants are preferably selected from fillers, colorants, coloured indicators. Preservatives include propyl gallate.

Preferably a composition comprises, by weight percent:
Part A:
one or more prepolymers (i) (80-99%)
blowing agent (0-10%)
a catalyst (>0-5%)
preservative (0-0.1%)
Part B:
one or more prepolymers (i) (60-69%)
one or more prepolymers (ii) (29-35%)
a foam stabiliser (0-11%)
a catalyst inhibitor (0-0.1%)
preservative (0-0.1%)
diluent or viscosity modifier (0-75%).

Part A:B may be present in a 1:99:99:1, for example 30:70 to 99:1 volume % ratio, respectively with or without added diluent or viscosity modifier. Preferably Part A:Part B is present in 30:70 to 70:30 volume % ratio, more preferably 45:55 to 55:45, such as substantially 50:50. Preferably Parts A and B are of compatible viscosity enabling mixing and substantially complete reaction thereof. Suitably viscosity of Part A:Part B is in the range 6:1-1:8, preferably 5:1-1:5, more preferably substantially 1:1. Compositions of disparate viscosity may be mixed in devices with increased length mixing head for example. The sterilisation of a composition may induce some viscosity increase, and therefore the viscosity ratio is preferably that of the Parts post-sterilisation.

Preferably the composition comprises prepolymers which are relatively short in length compared to that of the intended sterilised prepolymer. Prepolymers undergo chain lengthening during irradiation to a desired final viscosity or density. Preferably the Part A prepolymer(s) having at least one alkenyl unit or moity per molecule are relatively short in length compared to that of the corresponding sterilised Part A prepolymer(s).

Preferably the respective sterilised Parts are of a viscosity suitable for mixing by hand within a period of up to 1 minute. In a particular advantage Part A and/or Part B may comprise shortened pre-polymers that will increase in molecular weight during sterilisation to give species with the desired properties following sterilisation. More particularly Part A and optionally Part B comprise pre-polymers of chain length determined such that an increase in molecular weight after irradiation sterilisation confers on the prepolymers a desired molecular weight, viscosity, rheology or the like following sterilisation. Most preferably Part A comprises such shortened pre-polymers. Shortening is preferably to a percentage corresponding to the percentage increase in molecular weight and viscosity of the Part during sterilisation. This percentage will vary according to the chemical nature of any given composition. For example for a polydiorganosiloxane composition, shortening of Part A prepolymers is typically to the extent to give a 9-11% reduction in viscosity and shortening of Part B prepolymers is typically to the extent to give a 17-23% reduction in viscosity.

A problem envisaged with dispensing low viscosity compositions in the lower part of the range 5-300 Pa*s is retaining the composition in position at an intended site until cure is complete. Low viscosity compositions tend to flow within or away from an intended site during the initial period of cure, if not contained. WO2004/108175 (Molnlycke Health Care AB) discloses the compounded problem encountered if the composition is affected by movements of the body, pressure or friction. Preferably the composition may have, on initial mixing, a viscosity within the range 10-120 Pa*s, more preferably within the range 20-80 Pa*s. The composition may comprise one or more fillers to confer thixotropic properties thereon. A suitable filler may be fumed silica, for example such as Wacker Chemie, Wacker HDK™. WO2004/108175 discloses Wacker HDK™ as especially effective for this purpose.

Prepolymers (i) and (ii) have cross-linking function, prepolymer (ii) may also cooperate with blowing agent to cause foaming.

More preferably a composition comprises, by part weight, a composition as recited in U.S. Pat. No. 5,153,231 example col 7 the contents of which are incorporated herein by reference, for example Cavi-Care:

| Ingredients | Parts by weight |
|---|---|
| Part A | |
| Dimethylvinylsilyl endblocked PDMS, viscosity 450 mm²/s, 0.01 mol % vinyl groups | 54 |
| Dimethylvinylsilyl endblocked PDMS, viscosity 9000 mm²/s, 0.002 mol % vinyl groups | 39 |
| Ethanol | 3 |
| Chloroplatinic acid | 4 |
| Propyl gallate | 0.01 |
| Part B | |
| Methyl butynol | 0.05 |
| Dimethylvinylsilyl endblocked PDMS, viscosity 450 mm²/s, 0.01 mol % vinyl groups | 10 |
| Dimethylvinylsilyl endblocked PDMS, viscosity 9000 mm²/s, 0.002 mol % vinyl groups | 54 |
| Trimethylsilyl endblocked polymethylhydrogensiloxane, viscosity 30 mm²/s, 1.5 mol % hydrogen | 16 |
| Polymethylhydrogen-PDMS, viscosity 5 mm²/s, 0.75 mol % hydrogen | 16 |
| Foam stabiliser-hexamethyldisiloxane coated polysilicates treated with the alcohol $F(CF_2)_8CH_2CH_2OH$ | 4 |
| Propyl gallate | 0.01 |

In a further aspect there is provided a method of preparing a composition as hereinbefore defined from its composition precursor comprising the steps of:
 combining prepolymers (i), (ii) and catalyst (iii) as hereinbefore defined to form at least one Part A and at least one Part B as hereinbefore defined; and
 sealing the Part(s) A and Part(s) B in receptacles with barrier polymer means as hereinbefore defined.

Preferably combining is with additional components, by weight percent as hereinbefore defined In a further aspect there is provided a method for the preparation of a sterile composition comprising subjecting at least one of Part A and Part B, provided in or on a thermally stable receptacle or support as hereinbefore defined to elevated temperature of 121 C or more for a period of up to 28 hours.

Sterilization is regarded as a special process because of the difficulty in verifying by retrospective testing that products which have been through a sterilisation cycle are in fact sterile. Sterilisation controls for medical devices are achieved by a combination of validated sterilisation processes, selection of packaging appropriate to the sterilisation process and the application of quality assurance principles to the control of microbial bioburden on raw materials, intermediates, finished products and the manufacturing environment.

The results are determined as the "bioburden" this being the population of viable microorganisms on a product and/or a package. A product is determined "sterile" if free from viable microorganisms.

A sterility assurance level (SAL) is given as the probability of a viable microorganism being present on a product unit after sterilisation. SAL is normally expressed as $10^{-n}$. Requirements for terminally sterilized devices to be labelled "sterile" are defined as a SAL of $10^{-6}$, or in other words that the theoretical probability of there being a viable microorganism present on a device is equal to or less than $1\times10^6$ (BS EN 556-1:2001 Sterilisation of medical devices—Requirements for terminally sterilised devices to be labelled sterile).

The sterilisation may be conducted at any combination of elevated temperature and time which achieves terminal sterility and which lies within the thermal stability temperature range of the receptacle(s) or support(s). Higher temperatures increase costs, but longer time periods can be less well tolerated by receptacles and supports.

A suitable sterilisation regime may be determined based on the following, although variations are possible:
 123° C.→24 hours—(i) and/or (ii)
 134° C.→6 hours—(i) and/or (ii)
 160° C.-100 minutes—(i) and/or (ii).

Preferably a suitable sterilisation regime is selected, whereby for a desired packaging material, a sterilisation temperature Td is less than or equal to the thermal instability threshold temperature of the packaging, eg the Vicat T, less 5° C., or for a given sterilisation temperature Td, a suitable packaging material has thermal instability threshold temperature of the packaging, eg the Vicat T, greater than or equal to Td+5° C. By reading across a suitable chart, a suitable sterilisation time for the sterilisation temperature can then be determined. A material whose maximum temperature and time threshold lies substantially below the thermal instability threshold temperature is not suitable for use in the invention. For a material whose values lie above the thermal instability threshold temperature, possible sterilisation conditions include decreased time or temperature. Alternatively a suitable sterilisation regime is selected having regard to Graph 2 hereinabove.

In a further aspect of the invention there is provided the medical or non-medical, dental or non-dental use of a composition or elastomer as hereinbefore defined. Such use includes use as dyes; preservatives; gels; foams; aerosols; pharmaceuticals; adhesives; encapsulants; hair/skin care; cosmetic use; dental use; release coatings; coatings; adhesives and sealants; wound care; skin care including scar reduction; cavity care; medical device encapsulation such as electronic device encapsulation for biomedical applications; mould making; orthopaedics; drug delivery systems including antimicrobial systems; haemostatic and pharmaceutical systems; nutrition including manufacture of foodstuffs; aerospace, marine and submarine applications; ecologically sensitive applications; confined or isolated organisms, or their habitats, or confined or isolated medium or atmosphere such as those having low immunity; sterile, clean or aseptic applications; germination or propagation of living matter such as plants or organisms; including manufacture and repair of equipment, apparatus or components for any of the above and in particular aerospace, submarine sterile, clean or aseptic, germination or propagation.

A medical use of particular advantage is as a foamable composition as hereinbefore defined. A foamable composition is particularly suited for use in wound therapy, more particularly for use as a wound filler or wound packing material or cavity foam dressing, most particularly in NPWT. The foamable composition is of particular advantage in that it may be used in a sterile field or environment. It is in this field, working on very severe wounds, that the advantages of a dispensable shapable foam are most relevant, and yet a non-sterile composition can not be used. Accordingly embodiments disclosed herein enable for the first time the use of a curable foam composition in a sterile field.

Embodiments of the foamable composition for use in wound care or wound therapy may be suitable for providing a porous cured three dimensional resiliently deformable body. This is of particular advantage in providing support for the wound whilst being compressible as the wound heals and closes.

Preferably the foamable composition provides an open-pore cured three dimensional body. In the case of a composition suited for NPWT, the open pore system allows the development of a negative pressure at the wound, transmitted through the open-pore foamed body. Wound fluids may be evacuated through the foamed body.

In foam based NPWT the wound cavity is filled or covered with a porous foam packing material and covered over and sealed with flexible sheet (a drape) that is fairly impermeable to fluids. In gauze based NPWT a corresponding procedure is followed but using gauze packing material in place of porous foam packing material. In combination dressing or preformed dressing based NPWT either procedure may be followed if gauze or foam are to be used. A vacuum line is inserted under or through the drape into the wound site and its distal end is connected to a vacuum source (commonly a pump). The wound cavity, enclosed by the drape and tissue, contracts under the force of atmospheric pressure and compresses the packing material visibly. Gross tissue movement ceases after a few tens of seconds and fluid flow from the wound (withdrawn from the tissue) ensues. The fluid is transmitted through the packing material and up the vacuum line to a collection receptacle positioned between the distal end of the vacuum line and the vacuum source. The wound packing material mechanically supports the tissue to which it is applied, and also allows the free flow of fluids away from the site when a vacuum is applied, even when compressed.

Porosity is a function of number of pores and their size. It can be conveniently measured as a function of volume increase. The foamable composition suitably delivers a foam having a volume increase compared to the composition in the range from 3 to 10. Volume increase may be regulated by choice and amount of foaming agent, but is also a function of the polymer. In a particular advantage certain polydiorganosiloxane compositions may deliver porosity which is eminently suitable for wound care applications. Preferably, the body is of very high free internal volume, e.g. 70% to 90%. Generally, the size of the pores affects the transmission of negative pressure. Therefore, the smaller the pores, the smaller the negative pressure which can be established and the shorter its duration as the foam is progressively compressed by surrounding tissue growth. However the larger the pore size the lower the tensile strength, and the lower the support which the foam is able to deliver.

In a preferred embodiment the pores are resilient to tissue contraction, and do not collapse under contraction, whereby negative pressure may be maintained. The composition suitably delivers a foamed cured material having resilience and tensile strength capable of withstanding negative pressure of more than—150 mmHg, preferably 60-120 mmHg such as 60-100 mmHg below ambient atmospheric pressure, or 80-120 mmHg below ambient atmospheric pressure without causing the foam to collapse.

Preferably a foamable composition is adapted to deliver a foam which is open at its interfaces with moist or wet surfaces, more preferably is a silicone composition. This creates the ideal material for generating a negative pressure at a wound surface whilst maintaining open communication with the wound itself. In a further advantage the composition is suitable for providing a cured porous three dimensional body of desired shape.

The polydiorganosiloxane composition is adapted to deliver negative pressure selectively to moist wound surfaces, for example via an aperture or valve which can be readily inserted directly at its sealed face remote from the wound surface or indirectly via a vacuum connection line connecting to such sealed face.

It will be appreciated that throughout this specification reference is often made to a wound. In this sense it is to be understood that the term wound is to be broadly construed and encompasses open and closed wounds in which skin is torn, cut or punctured or where trauma causes a contusion. A wound is thus broadly defined as any damaged region of tissue where fluid may or may not be produced. Examples of such wounds include, but are not limited to, incisions, lacerations, abrasions, contusions, burns, diabetic ulcers, pressure ulcers, stoma, surgical wounds, trauma and venous ulcers or the like. Certain embodiments of the present invention are not restricted to use with wounds as will be discussed in more detail hereinbelow. Use as a wound filling material, preferably a negative pressure wound therapy wound filling material as hereinbefore defined includes use on wounds selected from chronic, acute, traumatic, sub-acute and dehisced wounds, ulcers (such as pressure or diabetic), partial-thickness burns and flaps and grafts. These include open, moist, granulating wounds, preferably surgical wounds such as those resulting from excision of ulcers, cancerous tissue such as perianal and perineal wounds and the like. For optimum healing of such wounds, the wound should be prevented from closing in on itself and allowing fluids to accumulate, whilst at the same time allowing the tissue around the wound to progressively contract, and the wound to shrink. Wound filling materials in NPWT therefore function as a type of "stent", supporting the wound and holding it open.

Further medical or non medical uses for which the composition is particularly advantageous include use as an adhesive or sealant composition as hereinbefore defined. An adhesive or sealant composition is particularly suited for use in clean, aseptic or sterile applications, more particularly as an adhesive or sealant for clean aseptic storage or packaging of items such as medicaments, particularly packaging medicaments within a medical device, or nutritional items and the like, or in the repair and/or maintenance and/or manufacture of sterile, aseptic or clean devices or machinery.

Preferably the composition for use as an adhesive or sealant in sterile, clean or aseptic conditions is packaged within further barrier means as hereinbefore defined. Further barrier means provide a barrier to infection. The composition is therefore a double wrapped item, this allows for the removal of the first layer of sterile sealed packaging to reveal receptacles or supports such as cartridges for or incorporated in a syringe, adhesive strips and the like, which are completely sterile inside and out, facilitating entry into a sterile environment. The composition omitting a further barrier means would comprise a non-sterile external surface of receptacles or supports and associated barrier means. As it is not possible to sterilise the composition using standard conditions for medical apparatus as hereinbefore described, it would not be possible to take such a composition into a sterile field.

The adhesive or sealant composition is suitable for introducing into a clean or aseptic area and dispensing or releasing into contact with an item to be adhered or sealed. Optionally a closure means is applied thereto. For example a bead of sealant may be dispensed around the rim of a sterile bottle prior to application of a closure means, or to any surface which it is desired to seal. A closure means or other opposing or adjacent surface is suitably applied with application of light pressure thereby ensuring that a seal is produced between the rim and the lid or other opposing or adjacent surfaces. In this way a universal sterile sealant is made available to the surgeon or clinician, lab technician, food manufacturer or mechanic. The sealant may be provided in a bagged dual syringe applicator and dispensed though a static mixer at the point of use. In this way a sterile dispenser and sealant may be conveniently provided for the user.

Certain sealant composition may be useful for example in sealing medical dressings, is useful for example in restraining egress of wound exudate or ingress of infection, or providing a vacuum seal for NPWT application; or as an insitu sterile lid sealant for laboratory vials and other vessels (e.g. Petri dish lids, sample storage pots, bijou bottles, culture bottles, demijohns and dewars) under clean or aseptic techniques; or in the aseptic manufacture of packaged nutritional items such as for example foodstuffs including milk, fruit juice, egg; or in the repair and/or maintenance and/or manufacture of sterile, aseptic or clean devices or machinery and the like.

A sealant for medical dressings may be applied in any known or novel manner. WO 00/74738 (Guyuron) discloses use of silicone based RTV-2 compositions to seal wounds i.a to minimise potential infections. The sealant of the invention may suitably therefore be used by casting on top of the wound and surrounding skin and allowing to cure.

WO2004/108175 (Molnlycke Health Care AB) discloses use of silicone based RTV-2 compositions to disintegrating skin or skin around wounds i.a to minimise potential infections and protect against harmful effects of wound exudate. The sealant is used by applying to skin about a wound, or to disintegrating skin, applying an adhesive or non-adhesive dressing over the wound and in contact with the sealant and allowing to cure, or by applying to an adhesive or non-adhesive dressing, applying the dressing to a wound and allowing to cure. In either case the dressing is sealed to the skin about the wound. The composition presents an admirable improvement on these methods by providing the surgeon, clinician or patient with a sterile sealant for use in these known manners or modifications thereof.

Foodstuffs may be sealed within a container e.g. Tetra Pak as hereinbefore described. In this way the sealant may be provided in bulk for industrial scale automated mixing and dispensing (e.g. using robotic dispensing systems as supplied by Rampf Dosiertechnik GMBH) in aseptic conditions. Sterile bagged cartridges of the 2 components may be manufactured for insertion in the dispensing machine. In this way sterile cartridges of the 2 components may be provided for delivery into the aseptic manufacturing area and insertion into the dispensing machine.

In the repair and/or maintenance of machinery, particularly envisioned is the replacement of gaskets. Here the sealant may be applied to a flange area or sealing surface as a bead prior to the bringing together of the components to form a seal. This reduces the need to sterilise individual gaskets prior to introduction to the aseptic environment and may reduce the need for multiple gaskets to be purchased or manufactured. In the aseptic manufacture of devices or machinery, particularly envisioned is the manufacture of space craft, marine or submarine craft, or components thereof in order to meet planetary protection requirements. Here the sealant composition may be dispensed to create an insitu gasket as hereinbefore defined. Alternatively the foamable composition may be dispensed as anti vibration material or insulation for heat or electrical purposes. The sealant may be provided in a bagged dual syringe applicator and dispensed though a static mixer at the point of use. In this way a sterile dispenser and sealant may be conveniently provided for the user. Alternatively sterile bagged receptacles such as cartridges of the composition Parts may be provided for delivery into an aseptic manufacturing area and insertion into a dispensing machine.

In a further aspect there is provided a wound dressing comprising the foamable or foamed composition, adhesive or sealant or composition thereof as hereinbefore defined.

In a further aspect of the invention there is provided a method for dispensing or releasing, and curing a composition as hereinbefore defined, comprising dispensing into a desired location or aperture at curing temperature for curing time.

The composition may be manually mixed and dispensed. Alternatively any form of dispensing device may be employed.

In a further aspect of the invention there is therefore provided a composition dispensing device comprising a terminally sterile composition as hereinbefore defined. Preferably the device is a NPWT device. Suitably a device comprises a mixing head having means to receive 2 or more cartridges comprising Parts A and B. Cartridges are adapted to locate and lock in place in the device. A suitable device for NPWT is a double barrelled syringe suitable for loading with 40 g of pre-polymers and fitted with a mixing head.

In a further aspect of the invention there is provided a method of therapy comprising dispensing a sterile composition as hereinbefore defined, preferably terminally sterile, to the site of a wound in a sterile environment.

In a further aspect of the invention there is provided a method of therapy as hereinbefore defined which is a method of negative pressure wound therapy comprising dispensing a terminally sterile composition as hereinbefore defined directly or indirectly into a wound and allowing to foam and cure, sealing the wound including the foamed cured composition and optionally including a negative pressure connection means, and applying negative pressure to the wound.

The composition may be dispensed directly into an open wound cavity and covered or dispensed into a covered cavity via an aperture in the cover or dispensed into a mould and inserted into a wound cavity. An open-pore surface or recess of surface is generated which may be connected directly or indirectly to a negative pressure source.

Currently available wound fillers require removal and cleansing or changing on a regular basis, typically every 8, 12 or 24 hours, with the maximum recommended period for a dressing to remain in place being 48 hours in the case for example of foam, although up to 72 hours for black foam, and 72 hours in the case of gauze. After longer periods tissue in-growth may occur. In the case of foam the washed dressing may be reused for up to a week, but as wound healing progresses successively smaller fillers should be produced.

Preferably, the composition may be dispensed into a prepared wound in a sterile field and may remain in situ without the need to cleanse and replace because the shaping process is simplified and highly accurate, rather the used filler is discarded and a new filler is simply dispensed. The degree of tissue contraction which has taken place may be determined by monitoring a reduction in the negative pressure being delivered or by a decrease in the resilient deformation of the cured composition, and if sufficient contraction is observed, the cured composition may be removed and new composition dispensed into the wound for continued therapy. The foamable curable composition preferably has a pore structure which is capable of being compressed under moderate pressures, as tissue contracts, without pore collapse.

In a further aspect of the invention there is provided a method for treating a wound site comprising
- dispensing a terminally sterile foamable composition into at least a portion of the wound site, wherein the foamable composition forms a porous foam material that is capable of transmitting negative pressure;
- sealing the wound site with a substantially fluid-tight seal; and
- applying negative pressure to the wound site using a source of negative pressure connected to the wound site. Preferably the foamable composition comprises a first part and a second part. Preferably the method further comprises curing the composition prior to sealing the wound site.

Sealing may be performed after or prior to dispensing the terminally sterile foamable composition.

The method may comprise mixing the first and second parts of the terminally sterile foamable composition together prior to dispensing or the first and second parts may be mixed while being dispensed. Preferably the step of connecting a source of negative pressure to the wound site comprises connecting a conduit to the wound site through or under the fluid-tight seal. Preferably sealing the wound site comprises applying a fluid-tight drape over the wound site. Preferably the terminally sterile foamable composition is sterilized prior to dispensing by heating the first and second parts in a thermally stable receptacle or support at an elevated temperature in excess of 121 C for a period of up to 28 hours.

Preferably the terminally sterile foamable composition is a composition as hereinbefore defined.

Within this aspect of the invention there is provided a method for treating a wound site, comprising:
- dispensing a terminally sterile composition around at least a portion of the wound site, wherein the composition comprises a sealant capable of making a substantially fluid-tight seal;
- covering the wound site with a substantially fluid-tight drape, the drape contacting at least a portion of the dispensed terminally sterile composition and forming a fluid-tight seal over the wound; and
- applying negative pressure to the wound site using a source of negative pressure connected to the wound site.

Preferably the composition comprises a first part and a second part.

Preferably the method further comprises curing the composition during or after covering the wound site.

Preferably the method further comprises placing a filler such as foam, gauze or the like into the wound site.

The drape suitably comprises an aperture so as to connect the source of negative pressure. The aperture may be positioned centrally, to one side or at the perimeter of the drape. The method may further comprise creating at least one aperture into or under the drape so as to connect the source of negative pressure.

Preferably the terminally sterile composition is sterilized prior to dispensing by heating the first and second parts in a thermally stable receptacle or support at an elevated temperature in excess of 121 C for a period of up to 28 hours.

Preferably the terminally sterile foamable composition is a composition as hereinbefore defined.

Within this aspect of the invention there is provided a further method for treating a wound site, comprising:
- applying a dressing to a wound site
- releasing a first part of a terminally sterile composition from a support around at least a portion of the wound site and exposing the said part,
- exposing a second part of a terminally sterile composition supported on a fluid-tight drape
- covering the wound site with the drape, thereby contacting and adhering the exposed first and second parts and adhering the drape around the wound site; and
- applying negative pressure to the wound site using a source of negative pressure connected to the wound site. Further features of this method correspond to those described hereinabove.

It is envisaged that the negative pressure range for certain embodiments of the present invention may be between about −20 mmHg and −200 mmHg (note that these pressures are relative to normal ambient atmospheric pressure thus, —200 mmHg would be about 560 mmHg in practical terms). Aptly the pressure range may be between about −40 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

It will be appreciated that according to certain embodiments of the present invention the pressure provided may be modulated over a period of time according to one or more desired and predefined pressure profiles. For example such a profile may include modulating the negative pressure between two predetermined negative pressures P1 and P2 such that pressure is held substantially constant at P1 for a pre-determined time period T1 and then adjusted by suitable means such as varying pump work or restricting fluid flow or the like, to a new predetermined pressure P2 where the pressure may be held substantially constant for a further predetermined time period T2. Two, three or four or more predetermined pressure values and respective time periods may be optionally utilised. Aptly more complex amplitude/frequency wave forms of pressure flow profiles may also be provided eg sinusoidal, sore tooth, systolic-diastolic or the like etc.

In a further aspect of the invention there is provided a wound dressing comprising the foamed composition as hereinbefore defined. Preferably the wound dressing is a NPWT wound dressing.

In a further aspect of the invention there is provided a NPWT kit comprising a fluid-tight wound dressing, a dispensible or releasable terminally sterile curable composition and attachment means for a vacuum pump to supply a negative pressure to the dressing. Preferably the terminally sterile curable composition is a composition of the invention as hereinefore defined.

BRIEF DESCRIPTION OF THE DRAWINGS

Embodiments of the invention will now be illustrated in non limiting manner with reference to the Figures in which FIGS. 1A-2B illustrate a NPWT foam filler wound dressing;

FIGS. 3A-C and 7, 8, 9 and 10 illustrate the use and application of a dispensable sterile foam filler wound dressing onto a patient;

FIGS. 4A, 5 and 6 illustrate the a kit including a sealant composition and wound dressing;

FIGS. 11A to 15B illustrate the use and application of an embodiment of a wound cover kit, apparatus and sealant onto a patient.

DETAILED DESCRIPTION

Figure 5:
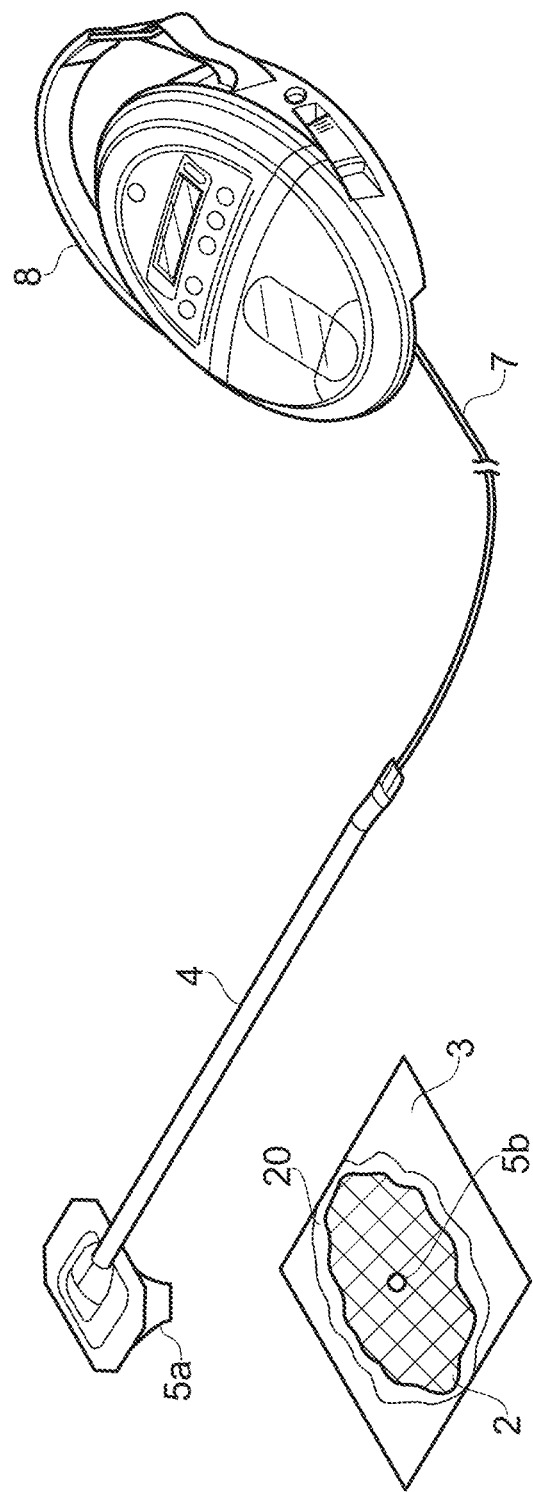

Referring now to FIG. 1, in conventional foam based NPWT the wound cavity (1) is filled or covered with a porous foam packing material (2), that may need to be cut to shape (2x shown as 2a) and covered over and sealed with an adhesive flexible sheet (a drape, 3) that is fairly impermeable to fluids.

Referring to FIG. 2, a vacuum line (4) is inserted (5) under or through the drape (3) into the wound site (1), in various embodiments this is received in a aperture or groove in the foam (6), or wrapped in gauze. The distal end (not shown) of vacuum line (4) is connected to a vacuum source (commonly a pump, not shown). The wound cavity, enclosed by the drape and tissue, contracts under the force of atmospheric pressure and compresses the packing material or dressing visibly. The system is however prone to vacuum leakage.

In FIG. 3A, a sterile foamable composition is shown (10) being dispensed from syringe (11) into wound site (1). In FIG. 3B, the composition cures once dispensed to form a foamed block (12) contacting the wound bed (1). In FIG. 3C, a drape (3) is placed thereover and sealed in place in conventional manner. Vacuum line (4) is inserted (5) through the drape (3) in conventional manner whereupon vacuum may be initiated via vacuum line (4). The wound cavity behaves in corresponding manner as described in relation to FIG. 2. This system improves the fit of the foam filler, and reduces the stresses placed on the adhesive sealing drape.

FIG. 4A illustrates a composition for use as a NPWT sealant. The sealant (20) is used by applying to skin about or around a wound site (1), or to disintegrating skin. Adhesive or non-adhesive drape (3) is applied, with optional dressing (not shown) over the wound (1) and in contact with the sealant (20) and the sealant is allowed to cure in contact with the drape. Vacuum line (4) is inserted through an aperture (5) in the drape (3) in conventional manner whereupon vacuum may be initiated via vacuum line (4). The sealant improves the quality of the negative pressure transmitted to the wound bed. FIG. 5 shows a variant of FIG. 4, in which the pump (8) is removably connected (5a) through aperture (5b) in the drape (3).

Figure 6:
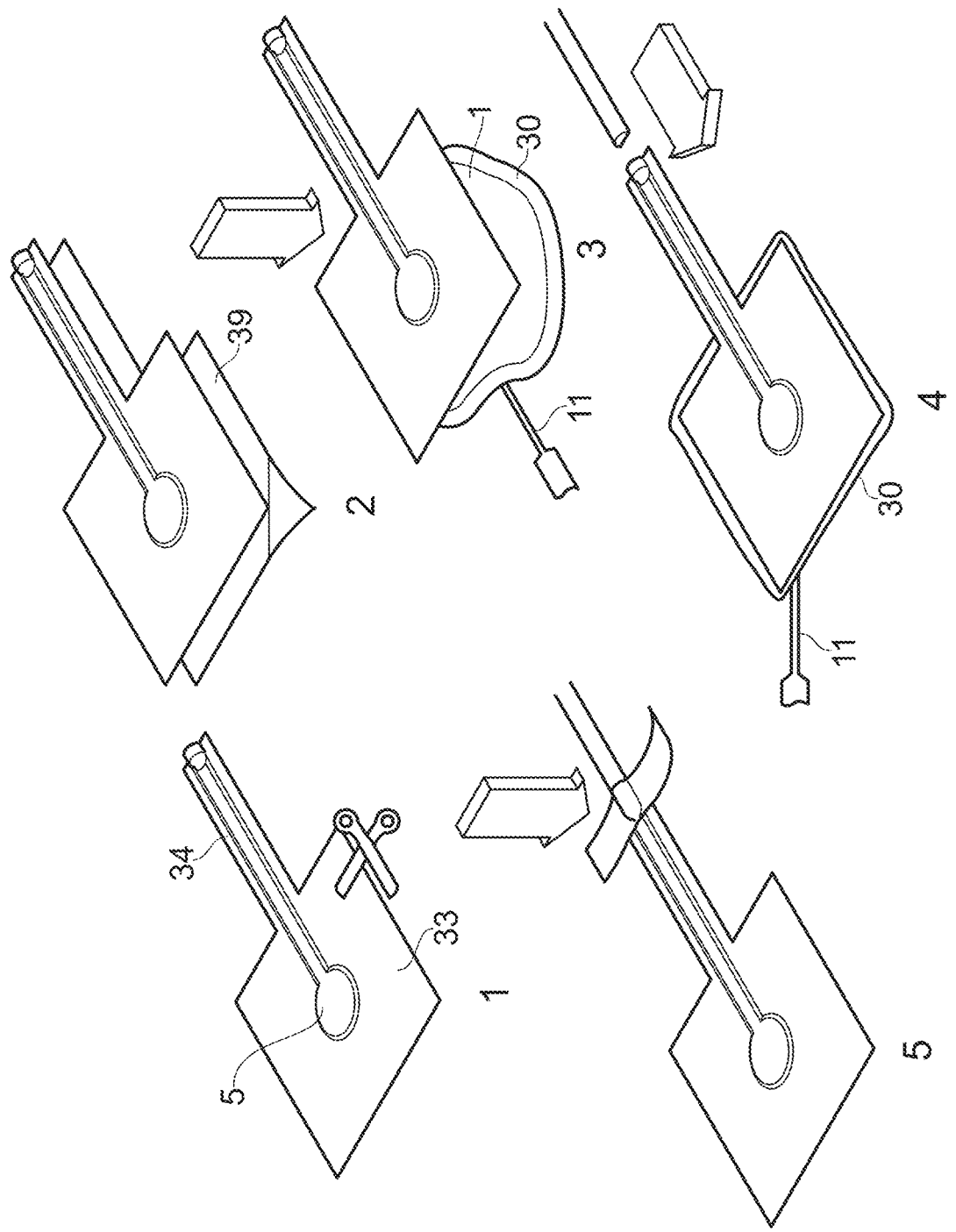
Figure 7:
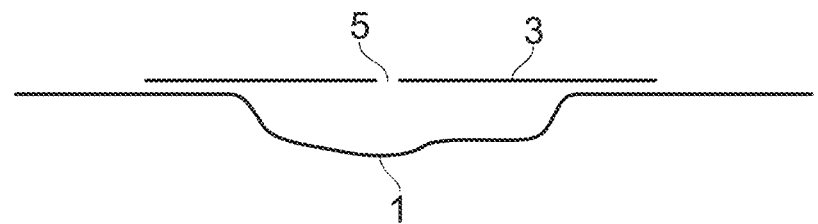
Figure 8:
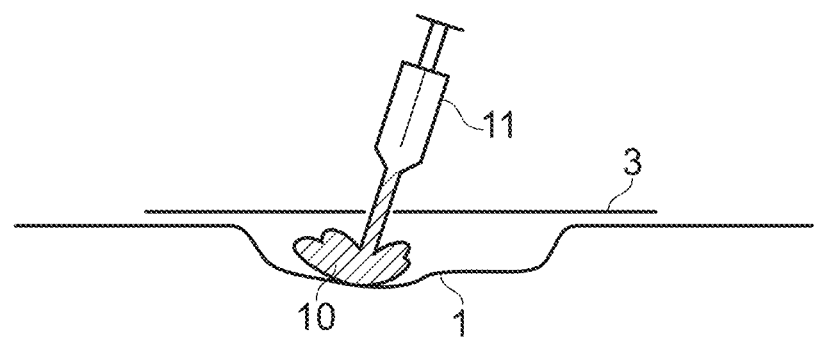
Figure 9:
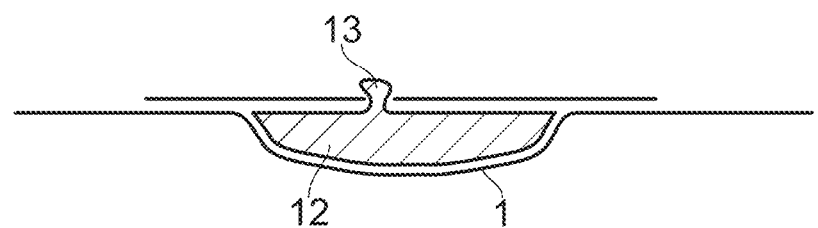

FIG. 6 shows a further variant in which preformed drape (33 incorporating integral vacuum line sheath (34) and aperture (5) is positioned over sealant (30) applied via syringe (11). In this case the drape (33) incorporates an adhesive backing (39), and sealant is therefore either dispensed about the wound in conventional manner as shown in step 3, or sealant (33) is dispensed to the edges of the adhered drape (33) as shown in step 4.

Figure 10:
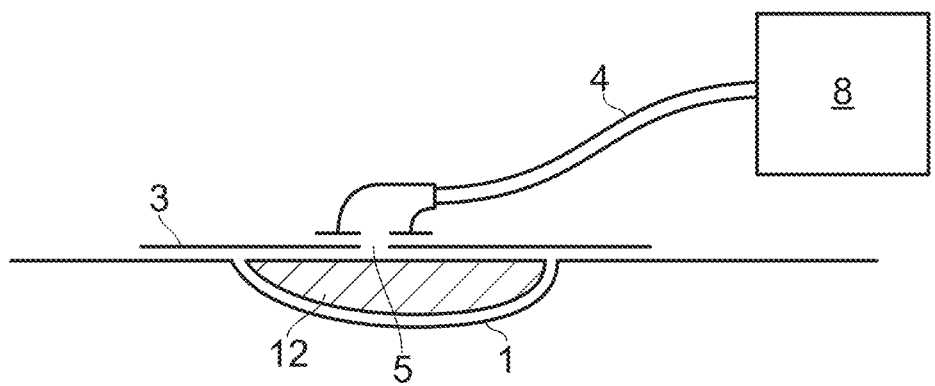
Figure 13B:
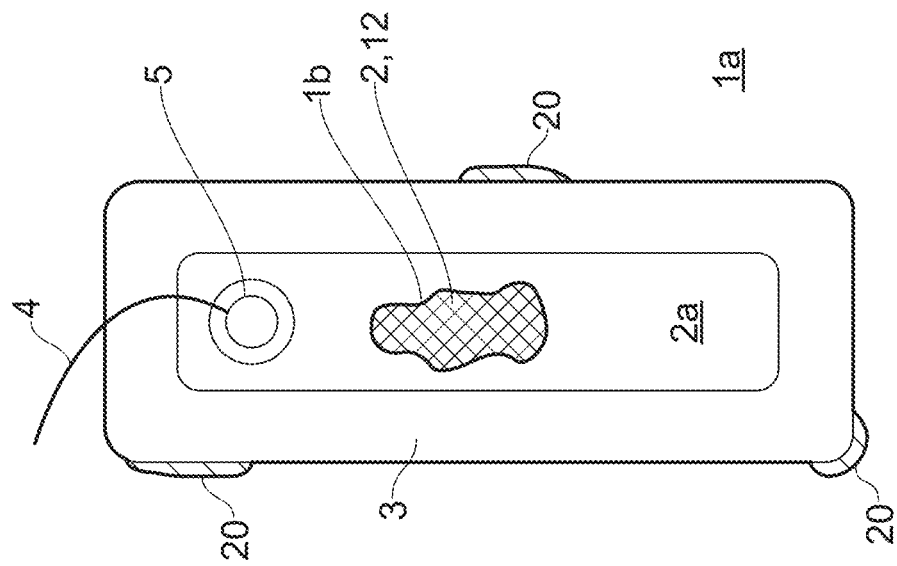
Figure 13A:
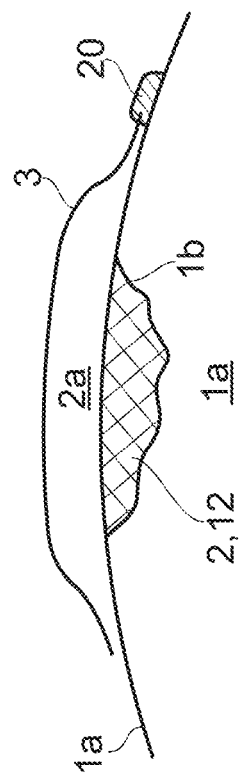

FIGS. 7 to 10 show a further variant to FIGS. 3A to 3C, in which the drape (3) is placed over the wound site (1) before composition (10) is dispensed from syringe (11) through aperture (5). The composition foams and cures to form a foamed block (12) including button (13) projecting through aperture (5). Button (13) is broken off to provide an aperture into the foam body. FIG. 10 shows vacuum line (4) coupled to aperture (5) and connected to vacuum pump (8) in conventional manner.

Figure 15B:
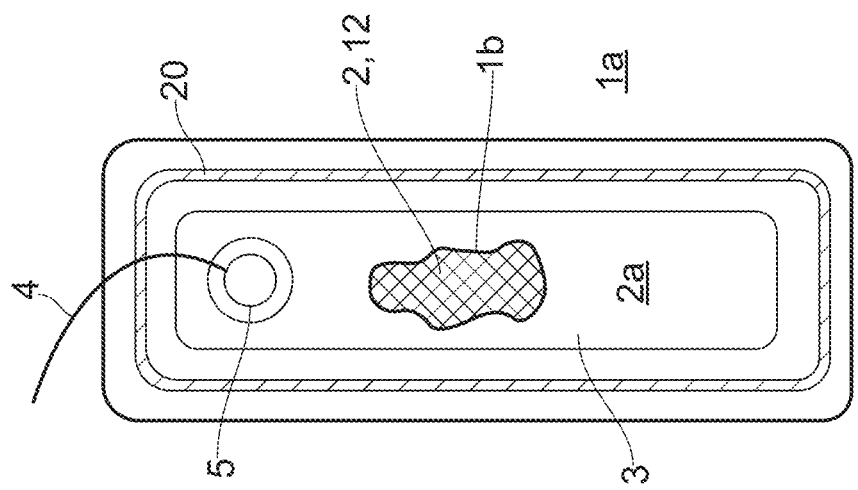
Figure 15A:
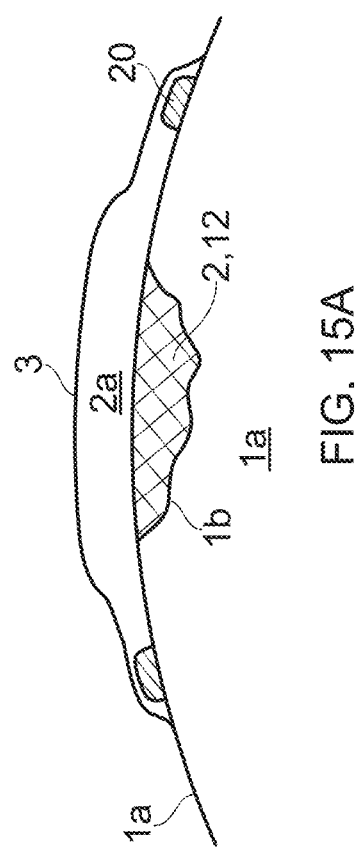
Figure 16:
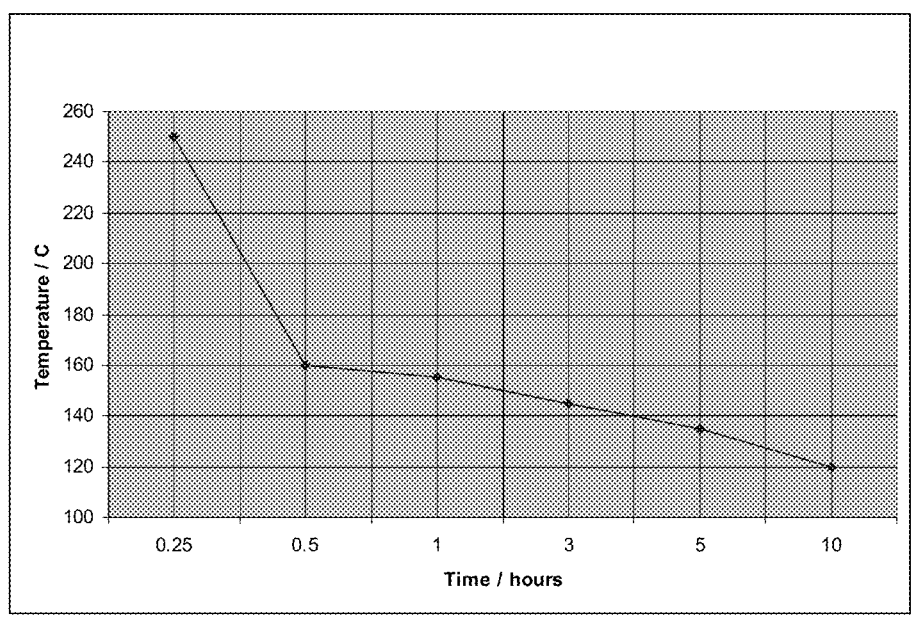
FIGS. 16 to 17 are graphs showing time and temperature of receptacles or supports.
Figure 17:
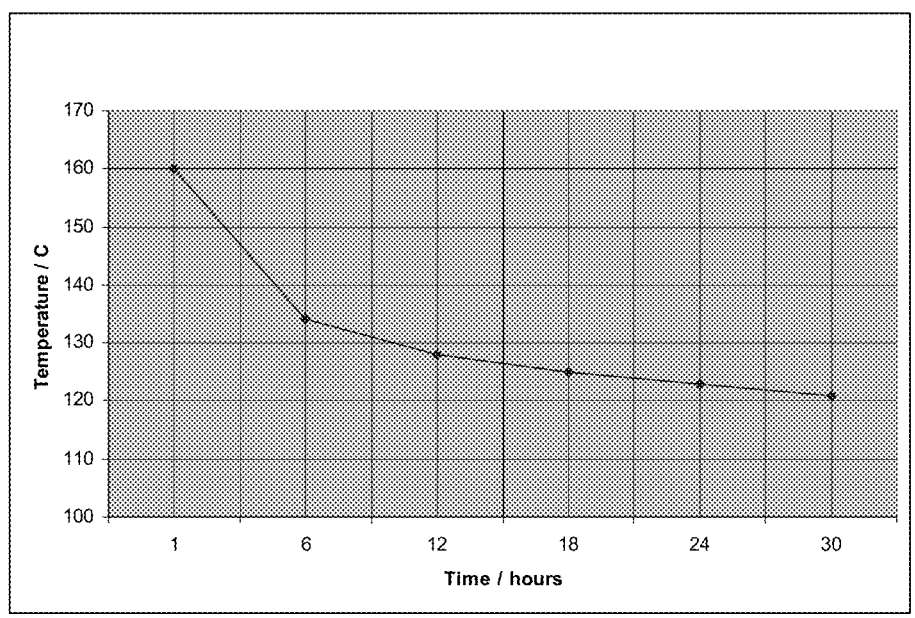

FIGS. 11 to 15 show variants to FIGS. 4a, 5 and 6, relating to dispensing sealant 20 to seal combination dressings/drapes (2a, 3) including integral port (5) for vacuum line (4). For these combination dressings (2a, 3) it is necessary to dispense the sealant (20) to the region of skin (1a) which will underly the perimeter portion of the drape (3) surrounding the dressing portion (2a), as shown in FIG. 15. In the case that it is difficult to prejudge where this perimeter portion will contact the skin (1a), dispensing about the edge of the combination dressing (2a, 3) is advantageous, as in FIGS. 11 and 12. Alternatively sealant (20) may be dispensed at the edge of the drape at positions where leakages can be observed or are suspected.

Alternatively sealant (20) may be dispensed directly to the combination dressing, also illustrated in FIG. 15, as a gasket (2), and the dressing then applied over the wound. In all cases, adhesive tape strips (3a) can be overlaid to ensure both adhesion and seal are satisfactory. In all cases, curing, sealing and operation of the vacuum are as previously described.

The invention may be carried into practice in various ways, and embodiments thereof will now be described by way of example only.

COMPARATIVE EXAMPLE

Example CE1

Preparation of Composition

RTV-2 polydimethylsiloxane composition Cavi-Care is a commercially available (Smith & Nephew, Catalogue number 4563) RTV-2 Pt catalysed foamable silicone elastomer having 30-105 seconds rise time, packaged as Parts A and B in a double foil laminate sachet laminated to either face with a PE, folded along the longitudinal axis, both parts of the sachet having a dispensing nozzle and a common tear notch in the folded edge. Part A contains predominantly two vinyl functionalised polydimethylsiloxanes and a platinum based catalyst. Part B contains predominantly vinyl functionalised polydimethylsiloxanes and a silicone based cross linking system. Both mixtures are clear to hazy moderately viscous liquids with a fill weight of 10.0-11.5 g. When mixed together the two chemical mixtures react to form a soft white, non absorbent foam dressing.

The sachet itself is made up of a laminate, used for the back and front, with a nominal thickness between 100 and 200 micron. It comprises 4 layers:

| | |
|---|---|
| PETP (polyethylene terephthalate) | 12 μm |
| ALU (aluminium) | 9 μm |
| OPA (biaxially oriented polymide) | 15 μm |
| LLDPE (linear low density polyethylene) | 75 μm |

Sterilisation—In an Oven

A Memmert oven was allowed to thermally equilibrate at the desired temperature (90° C., 100° C., 110° C., 120° C., 121° C., 123° C., 125° C., 127° C., 130° C., 136° C.). In each case a virgin pack of Cavi-Care was placed in the oven for 30 minutes (121° C. and 136° C. for 15 minutes), autoclaved using a liquid cycle, removed and the packaging integrity assessed.

After sterilisation the following were determined and compared with unsterilised polymer:

Subjective Assessment of Pack Integrity

A seal failure was observed when more than 2 crimps were separated when tested with the package tester.
  121° C./15 min: Packaging severely rippled and creased on the surface;
  136° C./15 min: Packaging soft and packaging heat seal failed;
  90° C. and 100° C./30 minutes: packaging integrity maintained;
  110° C./30 min: Part A inflated;
  120° C./30 min: Packaging soft but no silicone leakage;
  121° C./30 min: Packaging soft—seals delaminated in parts;
  123° C./30 min: Packaging soft—seals delaminated in parts;
  125° C./30 min: Packaging soft—possible seals failure at top of pack;
  127° C./30 min: Packaging failed—small amount of silicone leakage;
  130° C./30 min: Packaging failed—catastrophic seal failure with loss of containment of the silicones from both Part A and Part B.

The above investigations yielded the following:
  At 127° C. the packaging demonstrated catastrophic failure, the prepolymer leaking out of the packaging;
  At 110° C. the Part A packaging inflates, volatiles have been vaporised and put stress on the packaging allowing the possibility of contamination.

The Vicat softening temperature for typical low density poly(ethylenes) is reported as 88-100° C. (S. L Aggarwal, Polymer Handbook, ed. J. Brandrup and E. H. Immergut, Wiley Interscience, $2^{nd}$ edn., 1975, ch. V, pp 20-21.) with optical melting points for a series of selected poly(ethylenes) spanning the range 104.2° C. to 135.8° C.

The existing Cavi-Care packaging is therefore not suitable for use in an assessment where it will be subject to temperatures and cycle hold times in the range of 134° C. for 6 hours through to 123° C. for 24 hours as determined in the following examples.

Sterilisation—In an Autoclave

Cavi-Care was autoclaved using a liquid cycle (121° C. and 136° C. for 15 minutes).

121° C. After autoclaving at 121° C. for 15 minutes the packaging was severely rippled and creased on the surface.

After autoclaving at 136° C. for 15 minutes the packaging was soft and the packaging heat seals had failed.

Brookfield Viscosity

The effect of autoclaving on Cavi-Care prepolymer viscosity showed no substantial change.

Curing

The foam density and compressibility was evaluated with foam made by hand mixing parts A and B together using the spatulas and pots supplied with each Cavi-Care pack.

Foam Density and Compressibility

The effect of autoclaving on Cavi-Care cured foam density showed no change.

Sterility

Sterility was not investigated for Cavi-Care as the packaging disintegrated and this was therefore not a viable product—this type of sterilisation is not appropriate for a liquid non-aqueous system. If using heat for sterilisation, then a dry heat at 160 C can be used to properly sterilise the prepolymers. This type of sterilisation will be challenging for any packaging that is used.

Example 1

Thermally Stable Composition

Preparation of Composition

Example 1.1

Cavi-Care (see Comparative Example CE1 above) was repackaged by filling in sealed vials under argon, glass borosilicate vials and PP lid (stable to 140° C.) (Fischer Scientific, supplied by Schott-Duran, catalogue no. BTF-682-030H).

Example 1.2

Rhodorsil RTFoam 3240 NB (Bluestar Silicones) is a RTV-2 Pt catalysed foamable polydimethylsiloxane elastomer having 7.5 minutes rise time. This was packaged by filling in sealed vials under argon, glass borosilicate vials and PP lid (stable to 140° C.) (Fischer Scientific, supplied by Schott-Duran, catalogue no. BTF-682-030H).

Example 1.3

Rhodorsil NPWT was made by reformulating 1.2 to deliver faster rise time and cure, and foam properties differing in delivering lower volume, reduced density and increased tensile strength, although similar pore architecture. This was packaged by filling in sealed vials under argon, glass borosilicate vials and PP lid (stable to 140° C.) (Fischer Scientific, supplied by Schott-Duran, catalogue no. BTF-682-030H).

Sterilisation

As the Example 1 compositions do not contain a substantial amount of water, dry heat sterilisation conditions were examined. Time was allowed for chamber and samples to reach the target temperature before recording hold time. The hold time was therefore the time elapsed with contents at the target temperature.

The composition Example 1.2 was heated in an oven using a dry heat cycle at:
  S1a—121° C. for 1 hour;
  S1b—160° C. for 100.5 minutes;

As this regime reduces the number of packaging options available significantly lower temperatures were sought for the Example 1.2 composition:

S2—134° C. for 2.5 hours;

Example 1.3, Rhodorsil NPWT, was heated in an oven using a dry heat cycle at:

S3—134° C. for 6 hours.

S4—123° C. for 24 hours performed with inspection at 6 hour intervals

The following were determined and compared with unsterilised polymer:

Subjective Assessment of Pack Integrity

Packaging was intact and substantially unaffected by the sterilisation regime. No visible thermal damage or degradation.

Brookfield Viscosity

In all cases, parts A and B were of same or comparable viscosity.

Curing

After sterilisation each part was then mixed and foamed with a non-sterilised corresponding part and resultant foam properties observed.

Foam Density and Compressibility

The foam densities and compressibilities were evaluated with foam made by hand mixing parts A and B together using spatulas and pots supplied with each Cavi-Care pack.

Foam properties and rise time were same or comparable to unsterilised foam.

Example 1.3 Part A foamed with sterilised Part B and part B foamed with sterilised Part A each delivered foams with rise time of 2 to 3.25 minutes and substantially unaltered volume (a reduction of 8 to 10%).

Sterility Testing

The methodology employed was as follows:

D-value determination: Bacillus atrophaerus biological indicator (BI) wires (spore wires inoculated with Bacillus atrophaerus ATCC 9372, manufactured by Raven Labs, labelled population $3.4 \times 10^6$ cfu/wire, labelled dry heat d-value at 160° C. is 1.4 minutes) were used. Biological indicator population was verified. Composition to be tested was placed into respective capillaries, corresponding to the components to be packaged into respective receptacles as hereinbefore defined. Each capillary received a BI wire and was heat sealed thereby being made airtight. Population and D-value of capillaries was determined based on Raven method LW1-3100 Revision 3 for metal carriers (disinfect capillary outer surface, expose wire (Tween 80/glass beads), vortex, refrigerate, vortex, sonicate, dilute, heat-shock, cool, serial dilute, culture (Difco TSA/TSB, agar) and incubate, read at 24 hr, 48 hr (also 72 hr for thermally challenged spores) average the 48 hr counts and use to calculate the mean number of spores per BI). Log reduction was assessed based on population results from pre and post exposure.

Sterility

Sterility testing methodology described above was employed. The results were as follows:

Population Determination per capillary: 1.2A and 1.2B pre and post exposure (log reduction); nnr (number of negative replicates after 7 days incubation)

| Capillary | Pre/ x $10^6$ cfu | S1a/ x $10^6$ cfu (lr) | S1b/ x $10^6$ cfu (lr) | S2/ nnr |
|---|---|---|---|---|
| Control BI's | 12.665 | 16.200 | (6.4036) | 4/10 |
| 1.2A | 9.6676 | 8.9400 | (6.2863) | 0/10 |
| 1.2B | 9.5276 | 7.9800 | (6.2863) | 3/10 |

Lr = log reduction
Nnr = number of negative replicates after 7 days incubation

Population Determination per capillary: 1.3A and 1.3B pre and post exposure (log reduction); nnr (number of negative replicates after 7 days incubation)

| Capillary | Pre / x $10^6$ cfu | S3 / nnr | S4 / Nnr (6 hrs) | S4 / Nnr (12 hrs) | S4 / Nnr (18 hrs) | S4 / Nnr (24 hrs) |
|---|---|---|---|---|---|---|
| Control BI's | 25.800 | 10/10 | 10/10 | | | |
| 1.3A | 1.1025 | 10/10 | 0/5 | 0/5 | 2/5 | 5/5 |
| 1.3B | 9.8875 | 10/10 | 2/5 | 4/5 | 5/5 | 5/5 |

S1a-total survival (variation in counts withiin error margin);
S1b-"total kill" (at least 6 log reduction)-effective sterilisation;
S2-zero / partial kill (A, B and controls);
S3-"total kill"(at least 6 log reduction);
S4-"total kill"(at least 6 log reduction) at 24 hours (Parts A and B)
"total kill"(at least 6 log reduction) at 18 hours (Part B)
fractional kill at 18 hours (Part A)
fractional kill at 12 hours (Part B)
total survival at 12 hours (Part A)
fractional kill at 6 hours (Part B)
total survival at 6 hours (Part A)

Discussion

As can be seen clearly from the above, compositions 1.2 and 1.3 exposed to 134° C. for 6 hours (S3), 123° C. for 24 hours (S4) and 160° C. for 100.5 minutes (S1b) exhibited "total kill" (=6 log reduction) in comparison to their counterparts autoclaved at 134° C. for 2.5 hours (S2) and 121° C. for 1 hour (S1a).

Example 2

Thermally Stable Composition in Presence of Soft Packaging

Composition 1.3 was provided in a number of samples according to Example 1. Vials were contaminated each with a disc or ring of soft polymeric packaging materials found in tubing, stoppers, seals and the like, and subject to the heating regime according to Example 1 S3. Control vials uncontaminated were also subject to the S3 regime.

Subjective visual assessment and foaming investigation were conducted (Part A foamed with contaminated Part B, Part B foamed with contaminated Part A and contaminated Parts A and B foamed).

Of the 9 materials investigated:
contamination of vials by 3 translucent materials gave visually unchanged samples closely matching the rise time and rise volume profile of uncontaminated samples: Colourless: cured Elastosil LR 3003/50 (Wacker), cured Silpuran 6600/50 (Wacker), White: cured Thermolast MT Series TMSMED (Kraiburg TPE);
contamination of vials by 2 translucent white materials gave visually unchanged samples deviating slightly from the rise time and rise volume profile of uncontaminated samples: cured Thermolast MT/LF Series TM5 LFT (Kraiburg TPE) and Saint-Gobain Pperoxide Silicone Tubing (Saint-Gobain);

contamination of vials by 4 dark grey or black colored materials gave visually discolored darkened samples each of which either suffered an 11% to 30% increase in rise volume profile compared to uncontaminated samples, or suffered a 20 to 30 second increase in rise time: cured FM480 (Helvoet Pharma), cured FM257 (Helvoet Pharma), BSCF plunger stoppers (BD), NSCF plunger stoppers (BD)

Certain silicone rubber, peroxide silicone and styrene block copolymer materials are suitable as soft packaging materials for the compositions and methods disclosed herein, subject to individual testing as in Example 2

Certain bromobutyl and butadiene containing materials are considered unsuitable as soft packaging materials for compositions and methods disclosed herein, subject to individual testing as in Example 2.

COMPARATIVE EXAMPLE

Example CE2

Thermally Unstable Composition in Presence of Hard Packaging (Lids) and Enclosed Atmosphere Compositions 1.1 and 1.3 were provided in a number of samples according to Example 1. Borosilicate glass vials were sealed with a number of lids as shown in Table 3:

temperature resistant lid fitted with PTFE coated silicone seal—1.3 a) air headspace b) argon purge and headspace Aluminium screw cap lid with black rubber seal Polypropylene "wadless" lid.

Samples were subject to thermal cycle S4 as hereinbefore defined or of 130° C. for 24 hours (S5).

| Composition/ heat cycle | lid | Headspace/ purge | result |
| --- | --- | --- | --- |
| 1.1/S5 or S4 | PTFE coated silicon seal (Fischer Scientific, supplied by Schott-Duran, catalogue no. BTF-675-010C) | Air/none | A-heavily discolored, failed to foam, or inadequate foaming B-ok |
| 1.3/S4 | PTFE coated silicone seal (Fischer Scientific, supplied by Schott-Duran, catalogue no. BTF-675-010C). | Minimal/ Argon | A-heavily discolored B-ok |
| 1.1 S4 | Polypropylene (not temperature rated) | Air/none | A-no discoloration, foamed but reduced rise volume B-ok |
| 1.3/S3 | aluminium screw cap with black rubber seal | Air/none | A-heavily discolored B-ok |

-continued

| Composition/ heat cycle | lid | Headspace/ purge | result |
| --- | --- | --- | --- |
| 1.3/S3 | aluminium screw cap with black rubber seal | Argon/ Argon | A-discolored B-ok |
| 1.3/S3 | aluminium screw cap with black rubber seal | none/ Argon | B-minor discoloration |

Example 3

Thermally Stable Composition in Presence of Hard Packaging (Wadless Lids) and Enclosed Atmosphere Samples of 1.3 were subject to S3 heating cycle as follows:

Fisher 30 ml bottle (Fisher Scientific Catalogue no. BTF-605-030W) with polypropylene lid (not temperature rated)—a) air headspace b) argon purge and headspace Sterilin 30 ml bottle (Chromacol code 11912-001) with wadless lid—a) air headspace b) argon purge and headspace Schott Duran 25 ml bottle (Fisher Scientific Catalogue no. BTF-682-030H) with blue polypropylene lid (rated to 140° C.)—a) air headspace b) argon purge and headspace Following the cycle the samples displayed no black or coloured residue. The lids on the Sterilin bottles had melted, and caused catastrophic failure of inverted samples with loss of containment.

The Fischer lids had retained a seal but showed signs of a pressure build-up and had suffered permanent deformation.

The Schott Duran lids showed no outward signs of stress. 25 ml Schott Duran glass bottles with blue polypropylene lids (25/ISO thread, lid related autoclavable to 140 C, Fischer Scientific Catalogue no: BTF-682-030H) moulded from a single piece of polypropylene part with no additional elastomeric components, were shown to provide containment for the silicone prepolymers through the S3 heat sterilisation cycle, even when the bottles were inverted.

There was no loss of liquid containment and no visible degradation with this system following heating. As such this range of containers was selected as the most appropriate packaging system.

Example 4

Thermally Stable Composition in Presence of Hard Packaging (Lids) and Enclosed Atmosphere Example 1 highlighted the thermal stability of the composition under suitable sterilisation conditions, and also the requirement that the composition be provided in containment packaging which is thermally stable per se. Examples 2 and CE2 and 3 highlighted the additional requirement that the composition be provided in specific containment packaging which ensures that the composition is not contaminated by thermal sterilisation in presence of certain materials. This Example provides a detailed assessment of 1.1, 1.2 and 1.3 when heat treated at 123° C. for 24 hours (S4) and at 134° C. for 6 hours (S3) within a carefully contained packaging environment.

Pre-polymers A & B were dispensed into separate 100 ml bottles made of clear borosilicate glass (Schott Duran) with blue polypropylene lids (rated autoclavable to 140° C., Fisher Scientific, Product Code BTF-682-071Q). In each case 100 ml of pre-polymer was contained in each vessel. This fill volume afforded a reasonably modest headspace whilst providing sufficient separation between the upper surface of the pre-polymer and the lower surface of the lid such that the two did not make direct contact whilst under thermal load. Inert atmosphere conditions were imposed degassing with argon, sparging the pre-polymer and purging the headspace.

The influence of these heating conditions on the appearance of the pre-polymers and on selected functional performance characteristics of the foam curing process was assessed.

After heat treatment discrete changes in the visual appearance of 1.1 Part A and 1.2 Part B were observed. In the case of 1.1, some darkening occurred and in the case of 1.2 suspended agglomerates of a cloudy gel like species formed which settled on standing for 8 weeks. No visual changes were observed in either Part of 1.3 following either of the heat treatment regimes.

Discrete changes in functional performance were observed for the heat treated pre-polymers of 1.1, 1.2 and 1.3 when compared to their unheated controls. Subject to the desired performance requirements of the system these changes can be considered acceptable following treatment at both S4 and S3.

Preferably the conditions of S3 would be recommended for the heat sterilization of RTV-2 platinum catalysed addition cure silicone foam pre-polymers as these conditions were found to have the smallest effect on the visual appearance of the prepolymers and the smallest effect on the performance of the foaming reactions during cure.

The samples were allowed to stand for 8 weeks following heat treatment before the foaming reactions were assessed. To ensure thorough mixing following this hold period all samples were agitated by hand and then placed on a motorized roller to ensure thorough mixing of the contents.

For each composition both pre-polymer components (Part A and Part B) were transferred to a double barrelled mixing system (Double-Cartridge Prefilled Delivery System (S-System), MedMix Systems Ag). In each case a 25 ml 1:1 double barrelled cartridge was used. A cap was applied to the cartridge and the cartridge positioned vertically within a dye (typically a 150 ml Sterilin pot) on an electronic balance. One chamber was filled with Part A to 10 g±0.5 g. An equal volume of Part B was then filled into the opposing chamber and the height level of the menisci matched by eye.

The cartridge pistons were inserted, expelling the air headspace, so that they were flush with the surface of the pre-polymers. In this position they were locked and the unit placed in an internally dry container submerged within a water bath at 25° C. The units were allowed to thermally equilibrate at 25° C. for a minimum of 1 hour before use.

The assessment reactions were run in a laboratory with ambient temperature 20° C.±2° C. Any apparatus which would make direct contact with the chemicals during the dispensing or foaming steps was allowed to thermally equilibrate in this environment for a minimum of 1 hour (typically mixing heads and 150 ml Sterilin pots).

At point of use each cartridge had the tip cap removed, a 16 element helical static mixer applied and it was inserted into a ratcheted dispenser. The material was rapidly ejected into a transparent 150 ml Sterilin pot and a timer started at the point all of the material had been ejected from the dispensing unit.

Rise time was measured as the time taken to reach the maximum rise height. In the majority of cases this moment was punctuated by a bubble collapse running through the upper foam structure, this resulted in a slight but definite drop in the top surface of the foam.

Volume was measured using a liquid displacement method once a minimum of 10 minutes had been allowed to elapse after the rise time measurement. The headspace was filled with water and the volume of liquid measured in a 250 ml measuring cylinder. The silicone foam was then demoulded from the Sterilin pot, the Sterilin pot filled with water and the volume of liquid measured in a 250 ml measuring cylinder. The foam volume was calculated as the liquid displacement.

All foaming experiments were run in triplicate (n=3). The results are shown in Table 4.1

TABLE 4.1

|     | Rise time S4 | Rise time S3 | Foam volume S4 | Foam volume S3 |
| --- | --- | --- | --- | --- |
| 1.1 | −23% | +10% | −30% | −18% |
| 1.2 | −8% | −4% | −20 % | −10% |
| 1.3 | +8% | +12% | −10% | −8% |

Parts A and B treated, containment in glass bottles with PP lids.

Liquids sparged and headspaces purged with argon.

Percentage change in the mean rise times and mean foam volumes of heat treated samples relative to their unheated controls.

Some changes in visual appearance were noticed including 1.1 Part A darkening of the clear component, 1.2 Part B presence of suspended agglomerates in a cloudy gel. Properties of Parts A and B subject to S3 conditions were closest to the control properties. Both S3 and S4 conditions were considered acceptable, S3 conditions were recommended for heat sterilisation of RTV-2 prepolymers.

Example 5

Thermally Stable Sealant Compositions

Silpuran 2400/18 A/B (Wacker) is an addition-curing RTV-2 silicone rubber curing to a blue coloured silicone of low hardness. It has application in flexible moulding applications for prosthetics.

Silpuran 2400/18 pre-polymers A & B were dispensed into separate 100 ml bottles made of clear borosilicate glass (Schott Duran) with blue polypropylene lids (rated autoclavable to 140° C., Fisher Scientific, Product Code BTF-682-071 Q). In each case 100 ml of pre-polymer was contained in each vessel. This fill volume afforded a reasonably modest headspace whilst providing sufficient separation between the upper surface of the pre-polymer and the lower surface of the lid such that the two did not make direct contact whilst under thermal load. Inert atmosphere conditions were imposed degassing with argon, purging the headspace.

Materials were subject to heat treatment at 134° C. for 6 hours (S3) and 123° C. for 24 hours (S4). The samples were allowed to cool and conditioned overnight at a temperature of 20° C.±2° C. Viscosity was measured using a Brookfield Programmable RVDV-II+ Viscometer fitted with Spindle 7. A set speed of 100 rpm was used for Parts A and for Parts B. The spindle and temperature probe were thoroughly cleaned (using ethanol) and allowed to dry before each reading.

| | % change in viscosity relative to the un-heated control | |
|---|---|---|
| | Silpuran 2400/18 A | Silpuran 2400/18 B |
| 123° C., 24 hrs/cP | 11.36%* | 23.91%* |
| 134° C., 6 hrs/cP | 9.09%* | 17.39%* |

*Viscometer set speed 100 rpm

Curing was achieved by placing a 250 ml glass bottle with extra wide neck (Fisher Scientific, Product Code BTF-630-090N) on an electronic balance. In each case 100.00 g±0.10 g of Part A was weighed into the container. To this 100.00 g±0.30 g of the corresponding Part B was weighed directly into the container. Using a spatula the system was mixed by hand for 5 minutes and transferred to an oven pre-heated at 120° C. The system was cured at 120° C. for 1 hour. Samples were removed from the oven, allowed to cool and conditioned overnight at a temperature of 20° C.±2° C.

There were no significant differences in the visual appearance or in the surface tack (as gauged by touch) between the cured control sample and the cured samples made from pre-polymers subject to the S3 and S4 heating cycles.

Penetration was measured using a Setamatic Penetrometer with automatic release, timing device and standard 47.5 g plunger. The instrument was fitted with a hollow plastic cone with a stainless steel tip of mass 15 g. A dwell time of 60 seconds was used. All measurements were recorded in triplicate (n=3).

| | Relative mass of parts | | Mean penetration/ |
|---|---|---|---|
| | A | B | 1/10 mm |
| Silpuran 2400/18 A/B-control | 50.0% | 50.0% | 51 (SD 1) |
| Silpuran 2400/18 A/B-134° C., 6 hrs | 50.0% | 50.0% | 118 (SD 1) |
| Silpuran 2400/18 A/B-123° C., 24 hrs | 50.0% | 50.0% | 87 (SD 1) |

Subject to the desired performance requirements of the system these changes can be considered acceptable following treatment at both S3 and S4.

Example 6

Thermally Stable Sealant Compositions

Example 6a

Mepiseal™ (Molnlycke), a commercially available RTV-2 polyorganosiloxane sealant composition, was obtained as sold in a double barrel dispensing syringe dispensing 3 ml of composition. The cartridge has an integrated mixing head and integrated twist tip seal. The units are packaged within a secondary plastic bag. The composition is indicated for sealing a NPWT drape, and has an indicated cure time of 9 minutes.

Syringes incorporating composition were subject to S3 thermal sterilisation cycle and S4 thermal sterilisation cycle. Of these, 3 removed from their secondary pouches and 3 remaining in their secondary pouches were subject to S3. After 2.5 hours the plunger and piston were seen to have melted in all samples regardless of whether they were in the polymer pouches or not. After 6 hours no further change in the state of the syringes was observed. Other than the plungers, the remaining external components appeared intact. The pouches had not burst, although they had bonded to parts of the syringe inside. Upon opening one of these pouches it was observed that where the syringe had melted, direct contact could be made with the prepolymers. The prepolymers were no longer sealed in the syringe but were exposed. The viability and functional properties of the silicone prepolymers could not be assessed as it was not possible to dispense these from the syringe.

A further 4 samples were subject to S4 thermal sterilisation, 2 in their secondary pouches and 2 removed from their secondary pouches. After 24 hours the plungers did not fully melt however warping of the plungers was observed and the plungers moved freely in the barrel and no longer formed a seal. When compared to a non-heat sterilised Mepiseal™ syringe, it was observed that a colour change had occurred in the silicone prepolymers after being heat treated at both temperatures.

Manual kinetic time for the non-heat treated sample was 12 minutes and 20 seconds. The S4 heat treated composition was dispensed and allowed to cure and manual kinetic time tested by finger touch to the dispensed composition. If composition is found to transfer to the finger this indicates that the manual kinetic point has not been reached and the composition has not (fully) cured.

The experiment to determine manual kinetic time for the S4 heat treated sample was aborted after 72 hours as the manual kinetic point had not been reached.

The composition was therefore shown to be thermally unstable at S4 conditions, the mildest terminal sterilisation conditions which we had been able to achieve, as a result of failure of the packaging under S3 and S4 conditions. Packaging failure allowed exposure to air and moisture, due to rupture of the seal and this in turn led to contamination of the composition.

Example 6b

Mepiseal™ (Molnlycke), as in Example 7a was dispensed into 2 borosilicate glass vials and enclosed in manner according to Example 4 above and subject to S3 thermal sterilisation cycle. The composition was then mixed in standard manner and the manual kinetic time recorded. The manual kinetic time was considered acceptable following treatment at S3.

This indicates that the Mepiseal™ composition is thermally stable to conditions providing terminal sterility, if provided in thermally stable packaging in the absence of excess air.

Example 8

Thermally Stable Adhesive Compositions

Silpuran 2111 A/B (Wacker) is a commercially available 2-part, addition-curing silicone composition curing to a soft, tacky silicone adhesive. It is suitable for use in wound dressings.

Silpuran 2111 pre-polymers A & B were dispensed into separate 100 ml bottles made of clear borosilicate glass (Schott Duran) with blue polypropylene lids (rated autoclavable to 140° C., Fisher Scientific, Product Code BTF-682-071Q). In each case 100 ml of pre-polymer was contained in each vessel. This fill volume afforded a reasonably modest headspace whilst providing sufficient separation between the upper surface of the pre-polymer and the lower surface of the lid such that the two did not make direct contact whilst under thermal load. Inert atmosphere conditions were imposed degassing with argon, purging the headspace.

Materials were subject to heat treatment at 134° C. for 6 hours (S3) and 123° C. for 24 hours (S4). The samples were allowed to cool and conditioned overnight at a temperature of 20° C.±2° C. Viscosity was measured using a Brookfield Programmable RVDV-II+ Viscometer fitted with Spindle 7. A set speed of 100 rpm was used for Parts A and a set speed of 50 rpm was used for Parts B. The spindle and temperature probe were thoroughly cleaned (using ethanol) and allowed to dry before each reading.

% change in viscosity relative to the un-heated control

|  | Silpuran 2111 A | Silpuran 2111 B |
|---|---|---|
| 123° C., 24 hrs | 0.36%* | 1.47%† |
| 134° C., 6 hrs | 2.00%* | −0.15%† |

*Viscometer set speed 100 rpm

†Viscometer set speed 50 rpm

Curing was achieved by placing a 250 ml glass bottle with extra wide neck (Fisher Scientific, Product Code BTF-630-090N) on an electronic balance. In each case 100.00 g±0.10 g of Part A was weighed into the container. To this 100.00 g±0.30 g of the corresponding Part B was weighed directly into the container. Using a spatula the system was mixed by hand for 5 minutes and transferred to an oven pre-heated at 120° C. The system was cured at 120° C. for 1 hour. Samples were removed from the oven, allowed to cool and conditioned overnight at a temperature of 20° C.±2° C.

There were no significant differences in the visual appearance or in the surface tack (as gauged by touch) between the cured control sample and the cured samples made from pre-polymers subject to the S3 and S4 heating cycles.

Penetration was measured using a Setamatic Penetrometer with automatic release, timing device and standard 47.5 g plunger. The instrument was fitted with a hollow plastic cone with a stainless steel tip of mass 15 g. A dwell time of 60 seconds was used. All measurements were recorded in triplicate (n=3).

|  | Relative mass of parts | | Mean penetration/ |
|---|---|---|---|
|  | A | B | 1/10mm |
| Silpuran 2111 A/B-control | 50.0% | 50.0% | 200 (SD 3) |
| Silpuran 2111 A/B-134° C., 6 hrs | 50.1% | 49.9% | 206 (SD 3) |
| Silpuran 2111 A/B-123° C., 24 hrs | 50.0% | 50.0% | 211 (SD 4) |

Subject to the desired performance requirements of the system these changes can be considered acceptable following treatment at both S3 and S4.

Example 9

Thermally Stable NPWT Foamable Compositions

The cured foamed Example 1.2 composition Rhodorsil RT Foam 3240 was able to transmit a negative pressure with pressure drop, however this was not totally reproducible. In some cases the transmitted pressure would be acceptable for NPWT.

The modified Example 1.3 composition, Rhodorsil NPWT, delivered a cured foam which was able to transmit negative pressure for NPWT.

Certain embodiments provide a route to sterile RTV-2 compositions at temperatures below that of the accepted standard dry heat cycle which removes packaging constraints and thereby provides a route to commercially viable packaging.

It will be appreciated that various embodiments and applications of the composite are envisaged and are not limited to the embodiments and applications hereinbefore described but may be varied in construction, detail and application within the scope of the appended claims.

What is claimed is:

1. A method of preparing, the method comprising:
   providing a curable composition apportioned between at least one Part A and at least one Part B, the composition comprising:
   one or more alkenyl-containing prepolymers including at least one alkenyl moiety per molecule,
   one or more SiH-containing prepolymers including at least one SiH unit per molecule,
   a catalyst facilitating curing by addition of alkenyl-containing prepolymer to SiH-containing prepolymer, and
   a blowing agent configured to evolve gas as part of or during a curing reaction,
   wherein the Part A is sealed within a first receptacle and does not include the one or more SiH-containing prepolymers, and
   wherein the Part B is sealed within a second receptacle and does not include the catalyst; and
   heating the first receptacle containing Part A and the second receptacle containing Part B at an elevated temperature of 123° C. or higher for a period of 18 hours or longer, wherein the at least one Part A and the at least one Part B are terminally sterile and kept sealed within the first receptacle and the second receptacle without degrading or interacting with the first receptacle and the second receptacle, respectively, during or after heating.

2. The method of claim 1, wherein combining the at least one Part A and the at least one Part B when dispensing the at least one Part A and the at least one Part B causes the curable composition to mix and form a porous foam.

3. The method of claim 1, wherein heating is conducted in a conventional oven or autoclave.

4. The method of claim 1, wherein a sterility level of the curable composition after heating corresponds to a sterility assurance level (SAL) of $10^{-6}$ such that the theoretical probability of there being a viable microorganism present is equal to or less than $1\times10^{-6}$.

5. The method of claim 1, wherein at least one of the first receptacle or the second receptacle comprises materials selected from the group consisting of polycarbonates, polypropylene, polymethylpentene, cyclic olefin copolymers, metal foil, glass, solid phase silicone polymer and from composites, laminates and combinations thereof.

6. The method of claim 1, wherein the one or more alkenyl-containing prepolymers and the one or more SiH-containing prepolymers include silicones comprising siloxanes and modified siloxanes, polyurethanes (PU) comprising polyester and polyether urethanes, elastomeric polyether polyesters, polyglycolic acid, polyacetates comprising ethyl vinyl acetate, polyacrylate, polyacid derivatives of polysaccharides comprising carboxyalkylcellulose, carboxyalkylchitosan and copolymers thereof, and their hybrids comprising copolymers, entangled systems and mixtures thereof.

7. The method of claim 1, the one or more alkenyl-containing prepolymers and the one or more SiH-containing prepolymers comprise polyorganosiloxanes; and curing by addition of the alkenyl-containing prepolymer to the SiH-containing prepolymer further comprises curing between organohydrogensiloxane units and organoalkenylsiloxane units incorporated into polymeric, coplymeric, entagled, and mixed prepolymer systems.

8. The method of claim 1, wherein each of the at least one Part A, the at least one Part B, the first receptacle and the second receptacle are thermally stable at the elevated temperature of 123° C. for the period in excess of 18 hours.

9. The method of claim 1, wherein the blowing agent is selected from the group consisting of methanol, ethanol, n-propanol, isopropanol, n-butanol, 2-butanol, tert-butanol, n-hexanol, n-octanol, benzyl alcohol, 4-butanediol, 1,5-pentanediol, 1,7-heptanediol, silane including at least one silanol group, polysilane including at least one silanol group, water, and combination thereof.

10. The method of claim 2, wherein the porous foam comprises 70% to 90% free internal volume.

11. The method of claim 2, wherein the porous foam is resiliently deformable.

12. A method of preparing a sterile packaged curable composition selected from a wound packing material or filler which can be configured to the shape of a wound or an adhesive or sealant for a wound dressing, wherein the composition is an RTV (Room Temperature Vulcanization) composition which comprises two or more Parts, which is apportioned between at least one Part A and at least one Part B, the method comprising:

preparing a composition comprising:
   (i) one or more alkenyl-containing prepolymers having at least one alkenyl moiety per molecule,
   (ii) one or more SiH-containing prepolymers having at least one SiH unit per molecule, and additionally:
   (iii) a catalyst for curing by addition of the alkenyl-containing prepolymer of (i) to the SiH-containing prepolymer of (ii),
   wherein Part A incorporates an amount of the one or more alkenyl-containing prepolymers of (i), wherein the one or more alkenyl-containing prepolymers of (i) comprises one or more polydiorganosiloxane prepolymers having at least one organoalkenylsiloxane unit per molecule, and additionally the catalyst of (iii) for curing by addition of the prepolymer of (i) to the prepolymer of (ii), wherein Part A does not include the prepolymer of (ii); and
   wherein Part B incorporates an amount of the one or more alkenyl-containing prepolymers of (i), wherein the one or more alkenyl-containing prepolymers of (i) comprises one or more polydiorganosiloxane prepolymers having at least one organoalkenylsiloxane unit per molecule, together with the one or more SiH-containing prepolymers having at least one SiH unit per molecule of (ii), wherein the one or more SiH-containing prepolymers having at least one SiH unit per molecule comprises one or more polydiorganosiloxane prepolymers having at least one organohydrogensiloxane unit per molecule; wherein the volume and viscosity of Parts A and B may be approximately equal; wherein Part B does not include the catalyst of (iii);
   wherein the composition is non-foamable or is foamable comprising (iv) a blowing agent, selected from any agent which evolves gas or vapour as part of or during the curing reaction; and
   wherein the at least one Part A and at least one Part B are provided within or upon at least two respective receptacles or supports, and are adapted to be dispensed or released therefrom in cooperative manner facilitating intimate contact and curing thereof, wherein the receptacle(s) or support(s) and the at least one of Part A and Part B are thermally stable at elevated temperature of 123° C. for a period in excess of 18 hours wherein the composition is sterilised in a conventional oven or autoclave at ambient or elevated pressure with steam present, but the manner of packaging is resilient to steam penetration and thereby prevents steam contacting the composition directly, whereby the effective sterilization is a dry heat sterilization;
   sealing the Part(s) A and Part(s) B in receptacles with barrier means in a manner to prevent contamination thereof.

13. The method of claim 12, wherein the catalyst of (iii) is for curing by addition of the prepolymer of (i) organoalkenylsiloxane to the prepolymer of (ii) organosiloxane.

* * * * *